United States Patent
Hostetter et al.

(10) Patent No.: US 7,138,502 B2
(45) Date of Patent: Nov. 21, 2006

(54) **ANTIBODIES TO THE PROPEPTIDE OF *CANDIDA ALBICANS* AND METHODS OF USE**

(75) Inventors: Margaret K. Hostetter, Milford, CT (US); Denise Devore-Carter, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/964,858

(22) Filed: Sep. 28, 2001

(65) Prior Publication Data

US 2003/0096975 A1    May 22, 2003

Related U.S. Application Data

(60) Provisional application No. 60/237,082, filed on Sep. 28, 2000.

(51) Int. Cl.
*C07K 16/00* (2006.01)
*A61K 39/395* (2006.01)

(52) U.S. Cl. .................. 530/388.5; 530/388.1; 530/387.9; 424/141.1; 424/152.1; 424/172.1; 435/975

(58) Field of Classification Search .......... 530/387.9, 530/388.2, 388.1, 388.5, 387.1, 389.1, 824; 424/139.1, 141.1, 130.1, 152.1, 172.1; 435/975
See application file for complete search history.

(56) References Cited

U.S. PATENT DOCUMENTS

| | | | |
|---|---|---|---|
| 5,578,309 A | 11/1996 | Cutler et al. | 424/274.1 |
| 5,886,151 A | 3/1999 | Hostetter et al. | 530/371 |
| 6,346,411 B1 * | 2/2002 | Hostetter et al. | 435/254.11 |
| 6,774,219 B1 * | 8/2004 | Hostetter et al. | 530/388.5 |

OTHER PUBLICATIONS

Ellis RW. Vaccines. (Eds) Plotkin et al. W.B. Saunders Company, Philadelphia, Clhapter 29,pp. 568-575, 1988.*
White et al. J. Cell Biochem. Suppl. 0, p. 173, 1990.*
Hostetter et al. J. Cell Biochem. Suppl. 16F, p. 149, x110, 1991.*
Nakamura RM. Clin. Physiol. Biochem. 1: 160-172, 1983.*
Hostetter, "Review: Integrin-like Proteins in *Candida* spp. and Other Microorganisms", Fungal Genetics and Biology 28, 135-145 (1999).
Gale et al., "Linkage of Adhesion, Filamentous Growth, and Virulence in *Candida albicans* to a Single Gene, *INT1*", Science, vol. 279, Feb. 27, 1998, pp. 1355-1358.

* cited by examiner

*Primary Examiner*—S. Devi
(74) *Attorney, Agent, or Firm*—B. Aaron Schulman; Stites & Harbison PLLC

(57) ABSTRACT

Antibodies and agents which can bind to the propeptide of the Int1p protein of yeast microorganisms such as *Candida albicans* are provided which can be useful in methods for treating or preventing infections arising from such microorganisms. Microorganisms expressing the Int1p protein, such as *C. albicans* and *S. cerevisiae*, have shown an ability to immunomodulate host cells which allows infections of these microorganisms to thrive and become virulent. The peptide regions involved in the activation of the Int1p protein are isolated and targeted so as to provide a method of disrupting activation and allow for treatment or prevention of infection by microorganisms expressing the int1p protein. In one preferred embodiment of the invention, an antibody or agent which can bind to the propeptide of the Int1p protein from *C. albicans* is utilized in methods to prevent or treat infections caused by *C. albicans* or other microorganisms expressing the Int1p protein.

5 Claims, 14 Drawing Sheets

MNSTPSKLLPIDKHSHLQLQPQSSSASIFNSPTKPLNFPRTNSKPSLDPNSSSDT
YTSEQDQEKGKEEKKDTAFQTSFDRNFDLDNSIDIQQTIQHQQQQPQQQQQLS
QTDNNLIDEFSFQTPMTSTLDLTKQNPTVDKVNENHAPTYINTSPNKSIMKKATPK
ASPKKVAFTVTNPEIHHYPDNRVEEEDQSQQKEDSVEPPLIQHQWKDPSQFNYS
DEDTNASVPPTPPLHTTKPTFAQLLNKNNEVNSEPEALTDMKLKRENFSNLSLDE
KVNLYLSPTNNNNSKNVSDMDSHLQNLQDASKNKTNENIHNLSFALKAPKNDIEN
PLNSLTNADISLRSSGSSQSSLQSLRNDNRVLESVPGSPKKVNPGLSLNDGIKGF
SDEVVESLLPRDLSRDKLETTKEHDAPEHNNENFIDAKSTNTNKGQLLVSSDDHL
DSFDRSYNHTEQSILNLLNSASQSQISLNALEKQRQTQEQEQTQAAEPEEETSFS
DNIKVKQEPKSNLEFVKVTIKKEPVSATEIKAPKREFSSRILRIKNEDEIAEPADIHP
KKENEANSHVEDTDALLKKALNDDEESDTTQNSTKMSIRFHIDSDWKLEDSNDG
DREDNDDISRFEKSDILNDVSQTSDIIGDKYGNSSSEITTKTLAPPRSDNNDKENS
KSLEDPANNESLQQQLEVPHTKEDDSILANSSNIAPPEELTLPVVEANDYSSFND
VTKTFDAYSSFEESLSREHETDSKPINFISIWHKQEKQKKHQIHKVPTKQIIASYQQ
YKNEQESRVTSDKVKIPNAIQFKKFKEVNVMSRRVVSPDMDDLNVSQFLPELSE
DSGFKDLNFANYSNNTNRPRSFTPLSTKNVLSNIDNDPNVVEPPEPKSYAEIRNA
RRLSANKAAPNQAPPLPPQRQPSSTRSNSNKRVSRFRVPTFEIRRTSSALAPCD
MYNDIFDDFGAGSKPTIKAEGMKTLPSMDKDDVKRILNAKKGVTQDEYINAKLVD
QKPKKNSIVTDPEDRYEELQQTASIHNATIDSSIYGRPDSISTDMLPYLSDELKKP
PTALLSADRLFMEQEVHPLRSNSVLVHPGAGAATNSSMLPEPDFELINSPARNVS
NNSDNVAISGNASTISFNQLDMNFDDQATIGQKIQEQPASKSANTVRGDDDGLA
SAPETPRTPTKKESISSKPAKLSSASPRKSPIKIGSPVRVIKKNGSIAGIEPIPKATH
KPKKSFQGNEISNHKVRDGGISPSSGSEHQQHNPSMVSVPSQYTDATSTVPDE
NKDVQHKPREKQKQKHHHRHHHHHKQKTDIPGVVDDEIPDVGLQERGKLFFR
VLGIKNINLPDINTHKGRFTLTLDNGVHCVTTPEYNMDDHNVAIGKEFELTVADSL
EFILTLKASYEKPRGTLVEVTEKKVVKSRNRLSRLFGSKDIITTKFVPTEVKDTWA
NKFAPDGSFARCYIDLQQFEDQITGKASQFDLNCFNEWETMSNGNQPMKRGKP
YKIAQLEVKMLYVPRSDPREILPTSIRSAYESINELNNEQNNYFEGYLHQEGGDC
PIFKKRFFKLMGTSLLAHSEISHKTRAKINLSKVVDLIYVDKENIDRSNHRNFSDVL
LLDHAFKIKFANGELIDFCAPNKHEMKIWIQNLQEIIYRNRFRRQPWVNLMLQQQ
QQQQQQQSSQQ

FIG. 1

```
   1 cccaaaaaag ataaaataaa aacaaaacaa aacaaaagta ctaacaaatt attgaaactt
  61 ttaattttta ataaagaatc agtagatcta ttgttaaaag aaatgaactc aactccaagt
 121 aaattattac cgatagataa acattctcat ttacaattac agcctcaatc gtcctcggca
 181 tcaatattta attccccaac aaaaccattg aatttcccca gaacaaattc caagccgagt
 241 ttagatccaa attcaagctc tgatacctac actagcgaac aagatcaaga gaaagggaaa
 301 gaagagaaaa aggacacagc ctttcaaaca tcttttgata gaaattttga tcttgataat
 361 tcaatcgata tacaacaaac aattcaacat cagcaacaac agccacaaca acaacaacaa
 421 ctctcacaaa ccgacaataa tttaattgat gaattttctt ttcaaacacc gatgacttcg
 481 actttagacc taaccaagca aaatccaact gtggacaaag tgaatgaaaa tcatgcacca
 541 acttatataa atacctcccc caacaaatca ataatgaaaa aggcaactcc taaagcgtca
 601 cctaaaaaag ttgcatttac tgtaactaat cccgaaattc atcattatcc agataataga
 661 gtcgaggaag aagatcaaag tcaacaaaaa gaagattcag ttgagccacc cttaatacaa
 721 catcaatgga agatccttc tcaattcaat tattctgatg aagatacaaa tgcttcagtt
 781 ccaccaacac caccacttca tacgacgaaa cctactttg cgcaattatt gaacaaaaac
 841 aacgaagtca atctggaacc agaggcattg acagatatga aattaaagcg cgaaaatttc
 901 agcaatttat cattagatga aaaagtcaat ttatatctta gtcccactaa taataacaat
 961 agtaagaatg tgtcagatat ggatctgcat ttacaaaact tgcaagacgc ttcgaaaaac
1021 aaaactaatg aaaatattca caatttgtca tttgctttaa aagcaccaaa gaatgatatt
1081 gaaaacccat taaactcatt gactaacgca gatattctgt taagatcatc tggatcatca
1141 caatcgtcat tacaatcttt gaggaatgac aatcgtgtct tggaatcagt gcctgggtca
1201 cctaagaagg ttaatcctgg attgtctttg aatgacggca taaagggggtt ctctgatgag
1261 gttgttgaat cattacttcc tcgtgactta tctcgagaca aattagagac tacaaaagaa
1321 catgatgcac cagaacacaa caatgagaat tttattgatg ctaaatcgac taataccaat
1381 aagggacaac tcttagtatc atctgatgat catttggact cttttgatag atcctataac
1441 cacactgaac aatcaatttt gaatcttttg aatagtgcat cacaatctca aatttcgtta
1501 aatgcattgg aaaaacaaag gcaaacacag gaacaagaac aaacacaagc ggcagagcct
1561 gaagaagaaa cttcgtttag tgataatatc aaagttaaac aagagccaaa gagcaatttg
1621 gagtttgtca aggttaccat caagaaagaa ccagttctgg ccacggaaat aaaagctcca
1681 aaaagagaat tttcaagtcg aatattaaga ataaaaaatg aagatgaaat tgccgaacca
1741 gctgatattc atcctaaaaa agaaaatgaa gcaaacagtc atgtcgaaga tactgatgca
1801 ttgttgaaga aagcacttaa tgatgatgag gaatctgaca cgacccaaaa ctcaacgaaa
1861 atgtcaattc gttttcatat tgatagtgat tggaaattgg aagacagtaa tgatggcgat
1921 agagaagata atgatgatat ttctcgttttt gagaaatcag atatttttgaa cgacgtatca
1981 cagacttctg atattattgg tgacaaatat ggaaactcat caagtgaaat aaccaccaaa
2041 acattagcac ccccaagatc ggacaacaat gacaaggaga attctaaatc tttggaagat
2101 ccagctaata atgaatcatt gcaacaacaa ttggaggtac cgcatacaaa agaagatgat
2161 agcatttag ccaactcgtc caatattgct ccacctgaag aattgacttt gcccgtagtg
2221 gaagcaaatg attattcatc ttttaatgac gtgaccaaaa cttttgatgc atactcaagc
2281 tttgaagagt cattatctag agagcacgaa actgattcaa aaccaattaa tttcatatca
2341 atttggcata aacaagaaaa gcagaagaaa catcaaaattc ataaagttcc aactaaacag
2401 atcattgcta gttatcaaca atacaaaaac gaacaagaat ctcgtgttac tagtgataaa
2461 gtgaaaatcc caaatgccat acaattcaag aaattcaaag aggtaaatgt catgtcaaga
2521 agagttgtta gtccagacat ggatgattg aatgtatctc aatttttacc agaattatct
2581 gaagactctg gatttaaaga tttgaattttt gccaactact ccaataacac caacagacca
2641 agaagttta ctccattgag cactaaaaat gtcttgtcga atattgataa cgatcctaat
```

*FIG. 2A*

2701 gttgttgaac ctcctgaacc gaaatcatat gctgaaatta gaaatgctag acggttatca
2761 gctaataagg cagcgccaaa tcaggcacca ccattgccac cacaacgaca accatcttca
2821 actcgttcca attcaaataa acgagtgtcc agatttagag tgcccacatt tgaaattaga
2881 agaacttctt cagcattagc accttgtgac atgtataatg atattttga tgatttcggt
2941 gcgggttcta aaccaactat aaaggcagaa ggaatgaaaa cattgccaag tatggataaa
3001 gatgatgtca agaggatttt gaatgcaaag aaaggtgtga ctcaagatga atatataaat
3061 gccaaacttg ttgatcaaaa acctaaaaag aattcaattg tcaccgatcc cgaagaccga
3121 tatgaagaat tacaacaaac tgcctctata cacaatgcca ccattgattc aagtatttat
3181 ggccgaccag actccatttc taccgacatg ttgccttatc ttagtgatga attgaaaaaa
3241 ccacctacgg ctttattatc tgctgatcgt tgttttatgg aacaagaagt acatccgtta
3301 agatcaaact ctgttttggt tcacccaggg gcaggagcag caactaattc ttcaatgtta
3361 ccagagccag attttgaatt aatcaattca cctgctagaa atgtgctgaa caacagtgat
3421 aatgtcgcca tcagtggtaa tgctagtact attagtttta accaattgga tatgaatttt
3481 gatgaccaag ctacaattgg tcaaaaaatc caagagcaac ctgcttcaaa atccgccaat
3541 actgttcgtg gtgatgatga tggattggcc agtgcacctg aaacaccaag aactcctacc
3601 aaaaaggagt ccatatcaag caagcctgcc aagctttctt ctgcctcccc tagaaaatca
3661 ccaattaaga ttggttcacc agttcgagtt attaagaaaa atggatcaat tgctggcatt
3721 gaaccaatcc caaaagccac tcacaaaccg aagaaatcat tccaaggaaa cgagatttca
3781 aaccataaag tacgagatgg tggaatttca ccaagctccg gatcagagca tcaacagcat
3841 aatcctagta tggtttctgt tccttcacag tatactgatg ctacttcaac ggttccagat
3901 gaaaacaaag atgttcaaca caagcctcgt gaaaagcaaa agcaaaagca tcaccatcgc
3961 catcatcatc atcatcataa acaaaaaact gatattccgg gtgttgttga tgatgaaatt
4021 cctgatgtag gattacaaga acgaggcaaa ttattcttta gagttttagg aattaagaat
4081 atcaatttac ccgatattaa tactcacaaa ggaagattca ctttaacgtt ggataatgga
4141 gtgcattgtg ttactacacc agaatacaac atggacgacc ataatgttgc cataggtaaa
4201 gaatttgagt tgacagttgc tgattcatta gagtttattt taactttgaa ggcatcatat
4261 gaaaaacctc gtggtacatt agtagaagtg actgaaaaga aagttgtcaa atcaagaaat
4321 agattgagtc gattatttgg atcgaaagat attatcacca cgacaaagtt tgtgcccact
4381 gaagtcaaag atacctgggc taataagttt gctcctgatg gttcatttgc tagatgttac
4441 attgatttac aacaatttga agaccaaatc accggtaaag catcacagtt tgatctcaat
4501 tgttttaatg aatgggaaac tatgagtaat ggcaatcaac caatgaaaac aggcaaacct
4561 tataagattg ctcaattgga agttaaaatg ttgtatgttc cacgatcaga tccaagagaa
4621 atattaccaa ccagcattag atccgcatat gaaagcatca atgaattaaa caatgaacag
4681 aataattact ttgaaggtta tttacatcaa gaaggaggtg attgtccaat ttttaagaaa
4741 cgttttttca aattaatggg cacttcttta ttggctcata gtgaaatatc tcataaaact
4801 agagccaaaa ttaatttatc aaaagttgtt gatttgattt atgttgataa agaaaacatt
4861 gatcgttcca atcatcgaaa tttcagtgat gtgttattgt tggatcatgc attcaaaatc
4921 aaatttgcta atggtgagtt gattgatttt tgtgctccta ataaacatga aatgaaaata
4981 tggattcaaa atttacaaga aattatctat agaaatcggt tcagacgtca accatgggta
5041 aatttgatgc ttcaacaaca caacaacaa caacaacaac aaagctccca acagtaattg
5101 aaaggtctac ttttgatttt tttaatttta attggcaaat atatgcccat tttgtattat
5161 cttttagtct aatagcgttt tctttttttc cagt

*FIG. 2B*

P DOMAIN SUBTILISIN MOTIFS

| | | | | | |
|---|---|---|---|---|---|
| Kex2 | D$_{179}$ | H$_{213}$ | N$_{314}$ | S$_{378}$ = | 199aa |
| | | | < R$_{318}$GD > | | |
| Furin | D$_{355}$ | H$_{395}$ | N$_{479}$ | S$_{555}$ = | 200aa |
| | | | < R$_{498}$GD > | | |
| Int1p | D$_{1022}$ | H$_{1064}$ | N$_{1146}$ | S$_{1236}$ = | 215aa |
| | | | < R$_{1149}$GD > | | |
| CD18 | D$_{290}$ | H$_{309}$ | N$_{351}$ | S$_{490}$ = | 200aa |
| | | | < R$_{397}$GD > | | |
| C3 | D$_{1245}$ | H$_{1289}$ | N$_{1327}$ | S$_{1430}$ = | 185aa |
| | | | < R$_{1393}$GD > | | |
| SpeB | D$_{135}$ | H$_{159}$ | N$_{295}$ | S$_{324}$ = | 189aa |
| | | | < R$_{307}$GD > | | |
| Fibrillin | D$_{930}$ | H$_{971}$ | N$_{1052}$ | S$_{1129}$ = | 199aa |
| | | | < R$_{1053}$GD > | | |
| EGF | D$_{219}$ | H$_{286}$ | N$_{312}$ | S$_{403}$ = | 184aa |
| | | | < R$_{363}$GD > | | |
| Fibronectin | D$_{1365}$ | H$_{1396}$ | N$_{1488}$ | S$_{1565}$ = | 200aa |
| | | | < R$_{1565}$GD > | | |

*FIG. 5*

COMPARISON OF THE HIGH AFFINITY HEPARIN-BINDING SITE OF
*MYCOBACTERIUM TUBERCULOSIS* HEPARIN-BINDING
HEMAGGLUTININ ADHESIN (HBHA) WITH THE PROPOSED
HEPARIN-BINDING SITE OF *CANDIDA ALBICANS* Int1p

HBHA     $\underline{K}_{180}$ AAA $\underline{KK}$ APA $\underline{KK}$ AAA $\underline{KK}_{195}$ Int1p    $\underline{K}_{155}$ SIM $\underline{KK}$ ATP $\underline{K}$ ASP $\underline{KK}_{169}$

*FIG. 6*

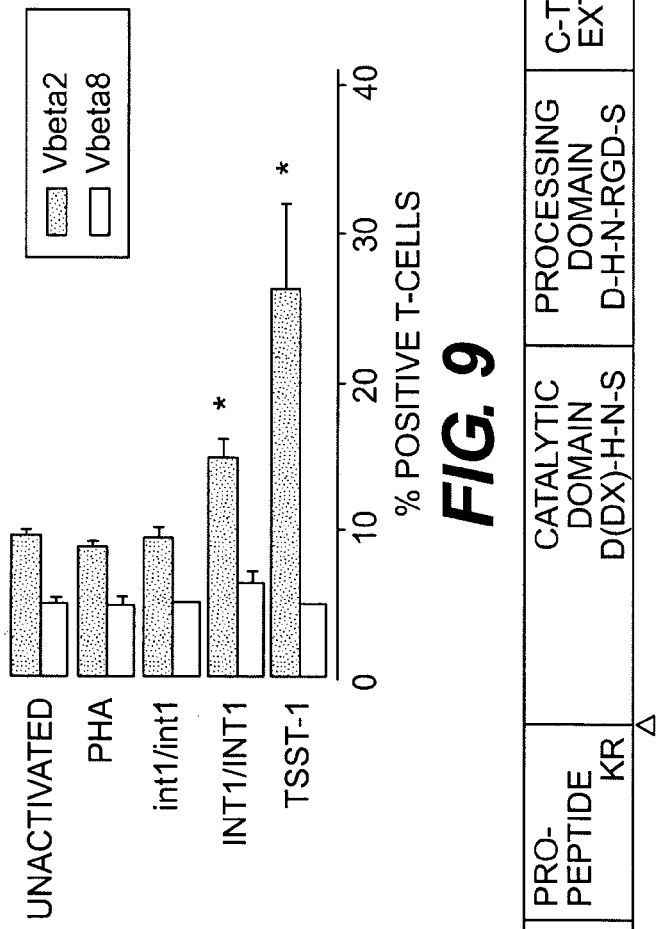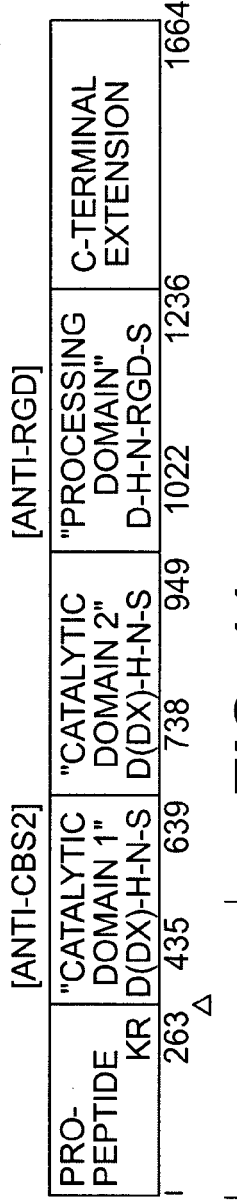

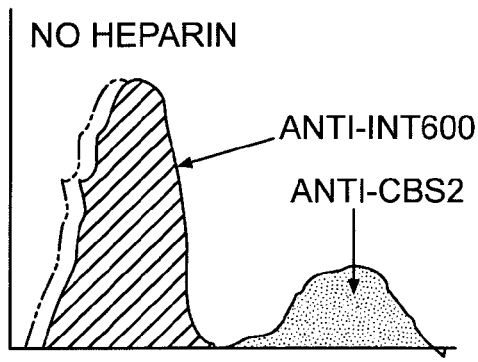
FIG. 12A
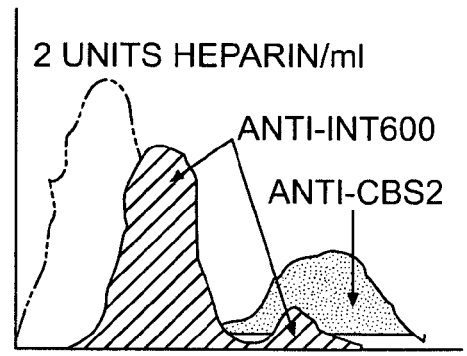
FIG. 12B
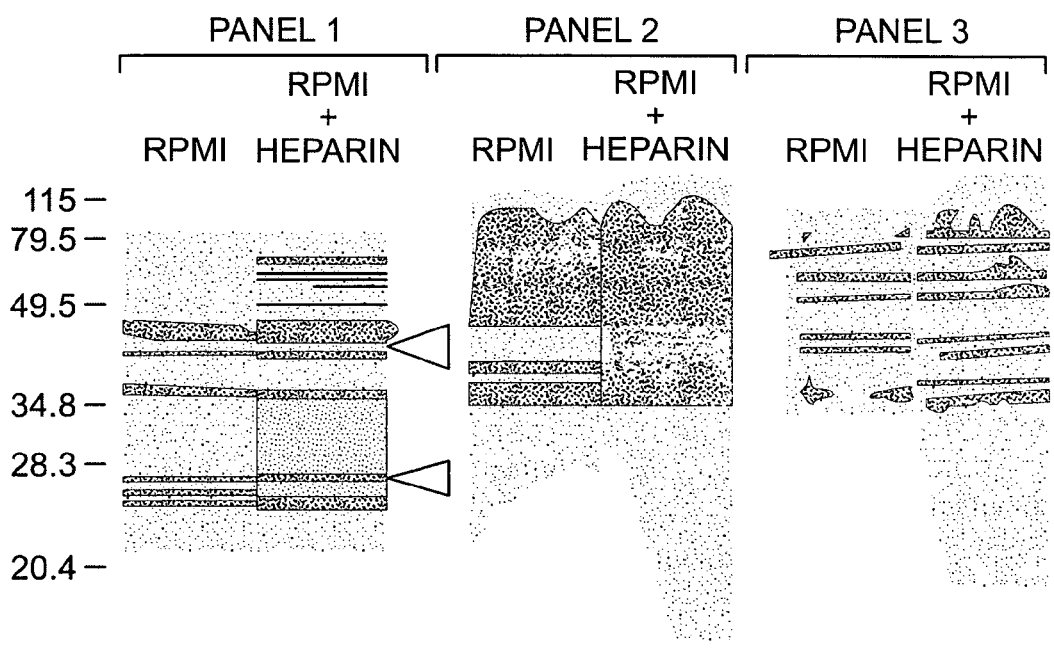
FIG. 13A     FIG. 13B     FIG. 13C

MODEL FOR THE PARTICIPATION OF INT1P IN CANDIDEMIA

MHC CLASS II-BINDING PEPTIDES

MAM $_{15}$FVQNL--NNVVFTNKELE$_{31}$

Int1p $_{239}$FAQLLNKNNEV--NSEPE$_{254}$

SEQUENCE LISTING

<160> NUMBER OF SEQ ID NOS: 13

<210> SEQ ID NO 1
<211> LENGTH: 1664
<212> TYPE: PRT
<213> ORGANISM: Candida albicans

<400> SEQUENCE: 1

```
Met Asn Ser Thr Pro Ser Lys Leu Leu Pro Ile Asp Lys His Ser His
1               5                   10                  15

Leu Gln Leu Gln Pro Gln Ser Ser Ser Ala Ser Ile Phe Asn Ser Pro
            20                  25                  30

Thr Lys Pro Leu Asn Phe Pro Arg Thr Asn Ser Lys Pro Ser Leu Asp
        35                  40                  45

Pro Asn Ser Ser Ser Asp Thr Tyr Thr Ser Glu Gln Asp Gln Glu Lys
    50                  55                  60

Gly Lys Glu Glu Lys Lys Asp Thr Ala Phe Gln Thr Ser Phe Asp Arg
65                  70                  75                  80

Asn Phe Asp Leu Asp Asn Ser Ile Asp Ile Gln Gln Thr Ile Gln His
                85                  90                  95

Gln Gln Gln Gln Pro Gln Gln Gln Gln Leu Ser Gln Thr Asp Asn
            100                 105                 110

Asn Leu Ile Asp Glu Phe Ser Phe Gln Thr Pro Met Thr Ser Thr Leu
        115                 120                 125

Asp Leu Thr Lys Gln Asn Pro Thr Val Asp Lys Val Asn Glu Asn His
    130                 135                 140

Ala Pro Thr Tyr Ile Asn Thr Ser Pro Asn Lys Ser Ile Met Lys Lys
145                 150                 155                 160

Ala Thr Pro Lys Ala Ser Pro Lys Lys Val Ala Phe Thr Val Thr Asn
                165                 170                 175

Pro Glu Ile His His Tyr Pro Asp Asn Arg Val Glu Glu Asp Gln
            180                 185                 190

Ser Gln Gln Lys Glu Asp Ser Val Glu Pro Pro Leu Ile Gln His Gln
        195                 200                 205

Trp Lys Asp Pro Ser Gln Phe Asn Tyr Ser Asp Glu Asp Thr Asn Ala
    210                 215                 220

Ser Val Pro Pro Thr Pro Pro Leu His Thr Thr Lys Pro Thr Phe Ala
225                 230                 235                 240
```

```
Gln Leu Leu Asn Lys Asn Asn Glu Val Asn Ser Glu Pro Glu Ala Leu
                245                 250                 255

Thr Asp Met Lys Leu Lys Arg Glu Asn Phe Ser Asn Leu Ser Leu Asp
            260                 265                 270

Glu Lys Val Asn Leu Tyr Leu Ser Pro Thr Asn Asn Asn Asn Ser Lys
        275                 280                 285

Asn Val Ser Asp Met Asp Ser His Leu Gln Asn Leu Gln Asp Ala Ser
    290                 295                 300

Lys Asn Lys Thr Asn Glu Asn Ile His Asn Leu Ser Phe Ala Leu Lys
305                 310                 315                 320

Ala Pro Lys Asn Asp Ile Glu Asn Pro Leu Asn Ser Leu Thr Asn Ala
                325                 330                 335

Asp Ile Ser Leu Arg Ser Ser Gly Ser Gln Ser Ser Leu Gln Ser
            340                 345                 350

Leu Arg Asn Asp Asn Arg Val Leu Glu Ser Val Pro Gly Ser Pro Lys
        355                 360                 365

Lys Val Asn Pro Gly Leu Ser Leu Asn Asp Gly Ile Lys Gly Phe Ser
    370                 375                 380

Asp Glu Val Val Glu Ser Leu Leu Pro Arg Asp Leu Ser Arg Asp Lys
385                 390                 395                 400

Leu Glu Thr Thr Lys Glu His Asp Ala Pro Glu His Asn Asn Glu Asn
                405                 410                 415

Phe Ile Asp Ala Lys Ser Thr Asn Thr Asn Lys Gly Gln Leu Leu Val
            420                 425                 430

Ser Ser Asp Asp His Leu Asp Ser Phe Asp Arg Ser Tyr Asn His Thr
        435                 440                 445

Glu Gln Ser Ile Leu Asn Leu Leu Asn Ser Ala Ser Gln Ser Gln Ile
    450                 455                 460

Ser Leu Asn Ala Leu Glu Lys Gln Arg Gln Thr Gln Glu Gln Glu Gln
465                 470                 475                 480

Thr Gln Ala Ala Glu Pro Glu Glu Thr Ser Phe Ser Asp Asn Ile
                485                 490                 495

Lys Val Lys Gln Glu Pro Lys Ser Asn Leu Glu Phe Val Lys Val Thr
            500                 505                 510

Ile Lys Lys Glu Pro Val Ser Ala Thr Glu Ile Lys Ala Pro Lys Arg
        515                 520                 525

Glu Phe Ser Ser Arg Ile Leu Arg Ile Lys Asn Glu Asp Glu Ile Ala
    530                 535                 540

Glu Pro Ala Asp Ile His Pro Lys Lys Glu Asn Glu Ala Asn Ser His
545                 550                 555                 560

Val Glu Asp Thr Asp Ala Leu Leu Lys Lys Ala Leu Asn Asp Asp Glu
                565                 570                 575

Glu Ser Asp Thr Thr Gln Asn Ser Thr Lys Met Ser Ile Arg Phe His
            580                 585                 590

Ile Asp Ser Asp Trp Lys Leu Glu Asp Ser Asn Asp Gly Asp Arg Glu
        595                 600                 605

Asp Asn Asp Asp Ile Ser Arg Phe Glu Lys Ser Asp Ile Leu Asn Asp
    610                 615                 620

Val Ser Gln Thr Ser Asp Ile Ile Gly Asp Lys Tyr Gly Asn Ser Ser
625                 630                 635                 640

Ser Glu Ile Thr Thr Lys Thr Leu Ala Pro Pro Arg Ser Asp Asn Asn
                645                 650                 655
```

-continued

```
Asp Lys Glu Asn Ser Lys Ser Leu Glu Asp Pro Ala Asn Asn Glu Ser
            660                 665                 670

Leu Gln Gln Gln Leu Glu Val Pro His Thr Lys Glu Asp Asp Ser Ile
            675                 680                 685

Leu Ala Asn Ser Ser Asn Ile Ala Pro Pro Glu Glu Leu Thr Leu Pro
            690                 695                 700

Val Val Glu Ala Asn Asp Tyr Ser Ser Phe Asn Asp Val Thr Lys Thr
705                 710                 715                 720

Phe Asp Ala Tyr Ser Ser Phe Glu Glu Ser Leu Ser Arg Glu His Glu
                725                 730                 735

Thr Asp Ser Lys Pro Ile Asn Phe Ile Ser Ile Trp His Lys Gln Glu
            740                 745                 750

Lys Gln Lys His Gln Ile His Lys Val Pro Thr Lys Gln Ile Ile
            755                 760                 765

Ala Ser Tyr Gln Gln Tyr Lys Asn Glu Gln Glu Ser Arg Val Thr Ser
            770                 775                 780

Asp Lys Val Lys Ile Pro Asn Ala Ile Gln Phe Lys Lys Phe Lys Glu
785                 790                 795                 800

Val Asn Val Met Ser Arg Arg Val Val Ser Pro Asp Met Asp Asp Leu
            805                 810                 815

Asn Val Ser Gln Phe Leu Pro Glu Leu Ser Glu Asp Ser Gly Phe Lys
            820                 825                 830

Asp Leu Asn Phe Ala Asn Tyr Ser Asn Asn Thr Asn Arg Pro Arg Ser
            835                 840                 845

Phe Thr Pro Leu Ser Thr Lys Asn Val Leu Ser Asn Ile Asp Asn Asp
            850                 855                 860

Pro Asn Val Val Glu Pro Pro Glu Pro Lys Ser Tyr Ala Glu Ile Arg
865                 870                 875                 880

Asn Ala Arg Arg Leu Ser Ala Asn Lys Ala Ala Pro Asn Gln Ala Pro
            885                 890                 895

Pro Leu Pro Pro Gln Arg Gln Pro Ser Ser Thr Arg Ser Asn Ser Asn
            900                 905                 910

Lys Arg Val Ser Arg Phe Arg Val Pro Thr Phe Glu Ile Arg Arg Thr
            915                 920                 925

Ser Ser Ala Leu Ala Pro Cys Asp Met Tyr Asn Asp Ile Phe Asp Asp
            930                 935                 940

Phe Gly Ala Gly Ser Lys Pro Thr Ile Lys Ala Glu Gly Met Lys Thr
945                 950                 955                 960

Leu Pro Ser Met Asp Lys Asp Val Lys Arg Ile Leu Asn Ala Lys
                965                 970                 975

Lys Gly Val Thr Gln Asp Glu Tyr Ile Asn Ala Lys Leu Val Asp Gln
            980                 985                 990

Lys Pro Lys Lys Asn Ser Ile Val Thr Asp Pro Glu Asp Arg Tyr Glu
            995                 1000                1005

Glu Leu Gln Gln Thr Ala Ser Ile His Asn Ala Thr Ile Asp Ser
         1010                1015                1020

Ser Ile Tyr Gly Arg Pro Asp Ser Ile Ser Thr Asp Met Leu Pro
         1025                1030                1035

Tyr Leu Ser Asp Glu Leu Lys Lys Pro Pro Thr Ala Leu Leu Ser
         1040                1045                1050

Ala Asp Arg Leu Phe Met Glu Gln Glu Val His Pro Leu Arg Ser
         1055                1060                1065

Asn Ser Val Leu Val His Pro Gly Ala Gly Ala Ala Thr Asn Ser
```

```
                    1070                1075                1080
Ser Met Leu Pro Glu Pro Asp Phe Glu Leu Ile Asn Ser Pro Ala
    1085                1090                1095

Arg Asn Val Ser Asn Asn Ser Asp Asn Val Ala Ile Ser Gly Asn
    1100                1105                1110

Ala Ser Thr Ile Ser Phe Asn Gln Leu Asp Met Asn Phe Asp Asp
    1115                1120                1125

Gln Ala Thr Ile Gly Gln Lys Ile Gln Glu Gln Pro Ala Ser Lys
    1130                1135                1140

Ser Ala Asn Thr Val Arg Gly Asp Asp Asp Gly Leu Ala Ser Ala
    1145                1150                1155

Pro Glu Thr Pro Arg Thr Pro Thr Lys Lys Glu Ser Ile Ser Ser
    1160                1165                1170

Lys Pro Ala Lys Leu Ser Ser Ala Ser Pro Arg Lys Ser Pro Ile
    1175                1180                1185

Lys Ile Gly Ser Pro Val Arg Val Ile Lys Lys Asn Gly Ser Ile
    1190                1195                1200

Ala Gly Ile Glu Pro Ile Pro Lys Ala Thr His Lys Pro Lys Lys
    1205                1210                1215

Ser Phe Gln Gly Asn Glu Ile Ser Asn His Lys Val Arg Asp Gly
    1220                1225                1230

Gly Ile Ser Pro Ser Ser Gly Ser Glu His Gln Gln His Asn Pro
    1235                1240                1245

Ser Met Val Ser Val Pro Ser Gln Tyr Thr Asp Ala Thr Ser Thr
    1250                1255                1260

Val Pro Asp Glu Asn Lys Asp Val Gln His Lys Pro Arg Glu Lys
    1265                1270                1275

Gln Lys Gln Lys His His His Arg His His His His His Lys
    1280                1285                1290

Gln Lys Thr Asp Ile Pro Gly Val Val Asp Asp Glu Ile Pro Asp
    1295                1300                1305

Val Gly Leu Gln Glu Arg Gly Lys Leu Phe Phe Arg Val Leu Gly
    1310                1315                1320

Ile Lys Asn Ile Asn Leu Pro Asp Ile Asn Thr His Lys Gly Arg
    1325                1330                1335

Phe Thr Leu Thr Leu Asp Asn Gly Val His Cys Val Thr Thr Pro
    1340                1345                1350

Glu Tyr Asn Met Asp Asp His Asn Val Ala Ile Gly Lys Glu Phe
    1355                1360                1365

Glu Leu Thr Val Ala Asp Ser Leu Glu Phe Ile Leu Thr Leu Lys
    1370                1375                1380

Ala Ser Tyr Glu Lys Pro Arg Gly Thr Leu Val Glu Val Thr Glu
    1385                1390                1395

Lys Lys Val Val Lys Ser Arg Asn Arg Leu Ser Arg Leu Phe Gly
    1400                1405                1410

Ser Lys Asp Ile Ile Thr Thr Thr Lys Phe Val Pro Thr Glu Val
    1415                1420                1425

Lys Asp Thr Trp Ala Asn Lys Phe Ala Pro Asp Gly Ser Phe Ala
    1430                1435                1440

Arg Cys Tyr Ile Asp Leu Gln Gln Phe Glu Asp Gln Ile Thr Gly
    1445                1450                1455

Lys Ala Ser Gln Phe Asp Leu Asn Cys Phe Asn Glu Trp Glu Thr
    1460                1465                1470
```

```
Met Ser Asn Gly Asn Gln Pro Met Lys Arg Gly Lys Pro Tyr Lys
    1475                1480                1485
Ile Ala Gln Leu Glu Val Lys Met Leu Tyr Val Pro Arg Ser Asp
    1490                1495                1500
Pro Arg Glu Ile Leu Pro Thr Ser Ile Arg Ser Ala Tyr Glu Ser
    1505                1510                1515
Ile Asn Glu Leu Asn Asn Glu Gln Asn Asn Tyr Phe Glu Gly Tyr
    1520                1525                1530
Leu His Gln Glu Gly Gly Asp Cys Pro Ile Phe Lys Lys Arg Phe
    1535                1540                1545
Phe Lys Leu Met Gly Thr Ser Leu Leu Ala His Ser Glu Ile Ser
    1550                1555                1560
His Lys Thr Arg Ala Lys Ile Asn Leu Ser Lys Val Val Asp Leu
    1565                1570                1575
Ile Tyr Val Asp Lys Glu Asn Ile Asp Arg Ser Asn His Arg Asn
    1580                1585                1590
Phe Ser Asp Val Leu Leu Leu Asp His Ala Phe Lys Ile Lys Phe
    1595                1600                1605
Ala Asn Gly Glu Leu Ile Asp Phe Cys Ala Pro Asn Lys His Glu
    1610                1615                1620
Met Lys Ile Trp Ile Gln Asn Leu Gln Glu Ile Ile Tyr Arg Asn
    1625                1630                1635
Arg Phe Arg Arg Gln Pro Trp Val Asn Leu Met Leu Gln Gln Gln
    1640                1645                1650
Gln Gln Gln Gln Gln Gln Gln Ser Ser Gln Gln
    1655                1660

<210> SEQ ID NO 2
<211> LENGTH: 5194
<212> TYPE: DNA
<213> ORGANISM: Candida albicans

<400> SEQUENCE: 2
cccaaaaaag ataaaataaa acaaaacaa  acaaaagta ctaacaaatt attgaaactt      60
ttaattttta ataagaatc  agtagatcta ttgttaaaag aaatgaactc aactccaagt    120
aaattattac cgatagataa acattctcat ttacaattac agcctcaatc gtcctcggca    180
tcaatattta attccccaac aaaaccattg aatttcccca gaacaaattc caagccgagt    240
ttagatccaa attcaagctc tgatacctac actagcgaac aagatcaaga gaaagggaaa    300
gaagagaaaa aggacacagc ctttcaaaca tcttttgata gaaattttga tcttgataat    360
tcaatcgata tacaacaaac aattcaacat cagcaacaac agccacaaca acaacaacaa    420
ctctcacaaa ccgacaataa tttaattgat gaattttctt ttcaaacacc gatgacttcg    480
actttagacc taaccaagca aaatccaact gtggacaaag tgaatgaaaa tcatgcacca    540
acttatataa atacctcccc caacaaatca ataatgaaaa aggcaactcc taaagcgtca    600
cctaaaaaag ttgcatttac tgtaactaat cccgaaattc atcattatcc agataataga    660
gtcgaggaag aagatcaaag tcaacaaaaa gaagattcag ttgagccacc cttaatacaa    720
catcaatgga agatccttc  tcaattcaat tattctgatg aagatacaaa tgcttcagtt    780
ccaccaacac caccacttca tacgacgaaa cctactttg  cgcaattatt gaacaaaaac    840
aacgaagtca atctggaacc agaggcattg acagatatga aattaaagcg cgaaaatttc    900
agcaatttat cattagatga aaaagtcaat ttatatctta gtcccactaa taataacaat    960
```

-continued

```
agtaagaatg tgtcagatat ggatctgcat ttacaaaact tgcaagacgc ttcgaaaaac    1020
aaaactaatg aaaatattca caatttgtca tttgctttaa aagcaccaaa gaatgatatt    1080
gaaaacccat taaactcatt gactaacgca gatattctgt taagatcatc tggatcatca    1140
caatcgtcat tacaatcttt gaggaatgac aatcgtgtct tggaatcagt gcctgggtca    1200
cctaagaagg ttaatcctgg attgtctttg aatgacggca taagggggtt ctctgatgag    1260
gttgttgaat cattacttcc tcgtgactta tctcgagaca aattagagac tacaaaagaa    1320
catgatgcac cagaacacaa caatgagaat tttattgatg ctaaatcgac taataccaat    1380
aagggacaac tcttagtatc atctgatgat catttggact cttttgatag atcctataac    1440
cacactgaac aatcaatttt gaatcttttg aatagtgcat cacaatctca aatttcgtta    1500
aatgcattgg aaaacaaag gcaaacacag gaacaagaac aaacacaagc ggcagagcct    1560
gaagaagaaa cttcgtttag tgataatatc aaagttaaac aagagccaaa gagcaatttg    1620
gagtttgtca aggttaccat caagaaagaa ccagttctgg ccacggaaat aaaagctcca    1680
aaaagagaat tttcaagtcg aatattaaga ataaaaaatg aagatgaaat tgccgaacca    1740
gctgatattc atcctaaaaa agaaaatgaa gcaaacagtc atgtcgaaga tactgatgca    1800
ttgttgaaga aagcacttaa tgatgatgag gaatctgaca cgacccaaaa ctcaacgaaa    1860
atgtcaattc gttttcatat tgatagtgat tggaaattgg aagacagtaa tgatggcgat    1920
agagaagata tgatgatat ttctcgtttt gagaaatcag atattttgaa cgacgtatca    1980
cagacttctg atattattgg tgacaaatat ggaaactcat caagtgaaat aaccaccaaa    2040
acattagcac ccccaagatc ggacaacaat gacaaggaga attctaaatc tttggaagat    2100
ccagctaata atgaatcatt gcaacaacaa ttggaggtac cgcatacaaa agaagatgat    2160
agcattttag ccaactcgtc caatattgct ccacctgaag aattgacttt gcccgtagtg    2220
gaagcaaatg attattcatc ttttaatgac gtgaccaaaa cttttgatgc atactcaagc    2280
tttgaagagt cattatctag agagcacgaa actgattcaa aaccaattaa tttcatatca    2340
atttggcata acaagaaaa gcagaagaaa catcaaaattc ataaagttcc aactaaacag    2400
atcattgcta gttatcaaca atacaaaaac gaacaagaat ctcgtgttac tagtgataaa    2460
gtgaaaatcc caaatgccat acaattcaag aaattcaaag aggtaaatgt catgtcaaga    2520
agagttgtta gtccagacat ggatgatttg aatgtatctc aattttttacc agaattatct    2580 gaagactctg gatttaaaga tttgaatttt gccaactact ccaataacac caacagacca    2640
agaagtttta ctccattgag cactaaaaat gtcttgtcga atattgataa cgatcctaat    2700
gttgttgaac ctcctgaacc gaaatcatat gctgaaatta gaaatgctag acggttatca    2760
gctaataagg cagcgccaaa tcaggcacca ccattgccac cacaacgaca accatcttca    2820
actcgttcca attcaaataa acgagtgtcc agatttagag tgcccacatt tgaaattaga    2880
agaacttctt cagcattagc accttgtgac atgtataatg atattttga tgatttcggt    2940 gcgggttcta aaccaactat aaaggcagaa ggaatgaaaa cattgccaag tatggataaa    3000
gatgatgtca agaggatttt gaatgcaaag aaaggtgtga ctcaagatga atatataaat    3060
gccaaacttg ttgatcaaaa acctaaaaag aattcaattg tcaccgatcc cgaagaccga    3120
tatgaagaat tacaacaaac tgcctctata cacaatgcca ccattgattc aagtatttat    3180
ggccgaccag actccatttc taccgacatg ttgccttatc ttagtgatga attgaaaaaa    3240
ccacctacgg ctttattatc tgctgatcgt ttgtttatgg aacaagaagt acatccgtta    3300
```

```
agatcaaaact ctgttttggt tcacccaggg gcaggagcag caactaattc ttcaatgtta    3360
ccagagccag attttgaatt aatcaattca cctgctagaa atgtgctgaa caacagtgat    3420
aatgtcgcca tcagtggtaa tgctagtact attagtttta accaattgga tatgaatttt    3480
gatgaccaag ctacaattgg tcaaaaaatc aagagcaac ctgcttcaaa tccgccaat    3540 actgttcgtg gtgatgatga tggattggcc agtgcacctg aaacaccaag aactcctacc    3600
aaaaaggagt ccatatcaag caagcctgcc aagctttctt ctgcctcccc tagaaaatca    3660
ccaattaaga ttggttcacc agttcgagtt attaagaaaa atggatcaat tgctggcatt    3720
gaaccaatcc caaagccac tcacaaaccg aagaaatcat tccaaggaaa cgagatttca    3780
aaccataaag tacgagatgg tggaatttca ccaagctccg gatcagagca tcaacagcat    3840
aatcctagta tggtttctgt tccttcacag tatactgatg ctacttcaac ggttccagat    3900
gaaaacaaag atgttcaaca caagcctcgt gaaaagcaaa agcaaaagca tcaccatcgc    3960
catcatcatc atcatcataa acaaaaaact gatattccgg gtgttgttga tgatgaaatt    4020
cctgatgtag gattacaaga acgaggcaaa ttattcttta gagttttagg aattaagaat    4080
atcaatttac ccgatattaa tactcacaaa ggaagattca ctttaacgtt ggataatgga    4140
gtgcattgtg ttactacacc agaatacaac atggacgacc ataatgttgc cataggtaaa    4200
gaatttgagt tgacagttgc tgattcatta gagtttattt taactttgaa ggcatcatat    4260
gaaaaacctc gtggtacatt agtagaagtg actgaaaaga agttgtcaa atcaagaaat    4320 agattgagtc gattatttgg atcgaaagat attatcacca cgacaaagtt tgtgcccact    4380
gaagtcaaag atacctgggc taataagttt gctcctgatg gttcatttgc tagatgttac    4440
attgatttac aacaatttga agaccaaatc accggtaaag catcacagtt tgatctcaat    4500 tgtttaatg aatgggaaac tatgagtaat ggcaatcaac caatgaaaag aggcaaacct    4560
tataagattg ctcaattgga agttaaaatg ttgtatgttc cacgatcaga tccaagagaa    4620
atattaccaa ccagcattag atccgcatat gaaagcatca atgaattaaa caatgaacag    4680
aataattact ttgaaggtta tttacatcaa gaaggaggtg attgtccaat ttttaagaaa    4740
cgttttttca aattaatggg cacttcttta ttggctcata gtgaaatatc tcataaaact    4800
agagccaaaa ttaatttatc aaaagttgtt gatttgattt atgttgataa agaaaacatt    4860
gatcgttcca atcatcgaaa tttcagtgat gtgttattgt tggatcatgc attcaaaatc    4920
aaatttgcta atggtgagtt gattgatttt tgtgctccta ataaacatga aatgaaaata    4980
tggattcaaa atttacaaga aattatctat agaaatcggt tcagacgtca accatgggta    5040
aatttgatgc ttcaacaaca acaacaacaa caacaacaac aaagctccca acagtaattg    5100
aaaggtctac ttttgatttt tttaatttta attggcaaat atatgcccat tttgtattat    5160
cttttagtct aatagcgttt tcttttttc cagt                                 5194
```

<210> SEQ ID NO 3
<211> LENGTH: 4
<212> TYPE: PRT
<213> ORGANISM: Candida albicans

<400> SEQUENCE: 3

Asp His Asn Ser
1

<210> SEQ ID NO 4
<211> LENGTH: 7
<212> TYPE: PRT

<213> ORGANISM: Candida albicans

<400> SEQUENCE: 4

Asp His Asn Arg Gly Asp Ser
1               5

<210> SEQ ID NO 5
<211> LENGTH: 5
<212> TYPE: PRT
<213> ORGANISM: Candida albicans

<400> SEQUENCE: 5

Phe Val Gln Asn Leu
1               5

<210> SEQ ID NO 6
<211> LENGTH: 11
<212> TYPE: PRT
<213> ORGANISM: Candida albicans

<400> SEQUENCE: 6

Asn Asn Val Val Phe Thr Asn Lys Glu Leu Glu
1               5                   10

<210> SEQ ID NO 7
<211> LENGTH: 11
<212> TYPE: PRT
<213> ORGANISM: Candida albicans

<400> SEQUENCE: 7

Phe Ala Gln Leu Leu Asn Lys Asn Asn Glu Val
1               5                   10

<210> SEQ ID NO 8
<211> LENGTH: 5
<212> TYPE: PRT
<213> ORGANISM: Candida albicans

<400> SEQUENCE: 8

Asn Ser Glu Pro Glu
1               5

<210> SEQ ID NO 9
<211> LENGTH: 15
<212> TYPE: PRT
<213> ORGANISM: Candida albicans

<400> SEQUENCE: 9

Lys Ser Ile Met Lys Lys Ala Thr Pro Lys Ala Ser Pro Lys Lys
1               5                   10                  15

<210> SEQ ID NO 10
<211> LENGTH: 4
<212> TYPE: PRT
<213> ORGANISM: Candida albicans

<400> SEQUENCE: 10

Lys Leu Arg Arg
1

<210> SEQ ID NO 11
<211> LENGTH: 16
<212> TYPE: PRT
<213> ORGANISM: Candida albicans -continued

```
<400> SEQUENCE: 11

Lys Ala Ala Ala Lys Lys Ala Pro Ala Lys Lys Ala Ala Lys Lys
1               5                   10                  15

<210> SEQ ID NO 12
<211> LENGTH: 15
<212> TYPE: PRT
<213> ORGANISM: Candida albicans

<400> SEQUENCE: 12

Lys Ser Ile Met Lys Lys Ala Thr Pro Lys Ala Ser Pro Lys Lys
1               5                   10                  15

<210> SEQ ID NO 13
<211> LENGTH: 6
<212> TYPE: PRT
<213> ORGANISM: Candida albicans
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Asp Asp Xaa His Asn Ser
1               5
```

ANTIBODIES TO THE PROPEPTIDE OF *CANDIDA ALBICANS* AND METHODS OF USE

CROSS-REFERENCE TO RELATED APPLICATIONS

The present application claims the benefit of U.S. provisional application Ser. No. 60/237,082, filed Sep. 28, 2000.

STATEMENT REGARDING FEDERALLY SPONSORED RESEARCH OR DEVELOPMENT

This invention was made with government support under Contract Number AI25827 awarded by the NIH. The government has certain rights in the invention.

FIELD OF THE INVENTION

The present invention relates in general to antibodies which can bind to the propeptide sequence of the Int1p protein of *Candida albicans* and methods of utilizing such antibodies to prevent and treat infections from microorganisms such as *C. albicans*, and in particular to agents and antibodies capable of disrupting the propeptide region or other subregions of the Int1p protein and the use of such agents and antibodies in the treatment and prevention of infection from yeasts such as *Candida albicans* and other microorganisms expressing the Int1p protein.

BACKGROUND OF THE INVENTION

The dimorphic yeast, *Candida albicans*, is the leading fungal pathogen in normal hosts and in patients with damaged immune systems. In normal hosts, disease caused by *C. albicans* ranges from mild, easily treated, superficial disease (e.g., thrush in newborn infants; paronychia in workers whose hands are immersed in water) to more severe, chronic or recurrent infections (e.g., candidal vaginitis). It is estimated that 5% of women of child-bearing age will suffer from recurrent candidal vaginitis (Hurley, *Proc. R. Soc. Med.* 70 (Suppl., 4), 1–8 (1970), and that virtually every woman will experience at least one episode during her reproductive years. Vaginitis is particularly frequent in otherwise normal females with diabetes or a history of prolonged antibiotic or oral contraceptive use. While short-term topical therapy is effective in treating individual episodes of vaginitis, such agents do not prevent recurrences. Thus, even in the normal host, infection with *C. albicans* can occur at epithelial surfaces, and recurrences are not prevented by presently available therapies.

In immunocompromised hosts such as cancer patients, transplant patients, post-operative surgical patients, premature newborns, or HIV-infected people, *C. albicans* ranks as the leading fungal pathogen. Invasion leading to systematic infection may also develop in neutropenic patients whose t-cell function is comprised. (Hostetter M K, *Clinical Microbiology Reviews*, January 1994, pp. 29–42.) In this population, disease ranges from aggressive local infections such as periodontitis, oral ulceration, or esophagitis in HIV-infected patients, to complex and potentially lethal infections of the bloodstream with subsequent dissemination to brain, eye, heart, liver, spleen, kidneys, or bone. Such grave prognoses require more toxic therapy, with attendant consequences from both the underlying infection and the treatment. Here again, the infection typically begins at an epithelial site, evades local defenses, and invades the bloodstream in the face of immunosuppression. Strategies to interrupt candidal adhesion therefore have broad applicability to the prevention of mild but recurrent disease in the normal host and to the reduction of substantial morbidity and mortality in the immunocompromised.

It is well recognized that *C. albicans* adheres to epithelial and endothelial cells in the human host, often times by recognizing proteins of the extracellular matrix called ligands. These ligands include proteins such as fibronectin, vitronectin, fibrinogen, the C3 degradation fragment iC3b, or the shorter C3 degradation fragment C3d. Because recognition of all of these proteins except C3d appears to be dependent upon the amino acid sequence ARGININE-GLYCINE-ASPARTIC ACID (or R-G-D), these candidal adhesions are thought to operate like the vertebrate integrins and are called "integrin-like proteins" or "integrin analogs."

Vertebrate integrins are composed of two subunits: an $\alpha$-subunit and a $\beta$-subunit. There are approximately 14$\alpha$ and 8$\beta$ subunits described to date in vertebrate cells. Using monoclonal or polyclonal antibodies to vertebrate integrins, several investigators have obtained evidence for integrin-like proteins in *C. albicans*.

One such protein is the protein Int1p of *Candida albicans*, and this protein has been observed to function as an adhesin, to participate in morphologic switching of blastospores to hyphae, and has been linked to virulence in mice. Rapid mortality ascribable to INT1/INT1 strains suggested that Int1p may have an immunomodulatory role. Pathogenesis studies using a mouse fungemia model have linked Int1p mediated adhesion and filamentation to *Candida albicans* virulence (Gale et al., *Science* 279:1355–1358, 1998), and intravenous inoculation of an int1/int1 double disruption mutant (CAG3) is associated with reduced mortality and renal inflammation compared to the wild type INT1/INT1 strain (CAF2) (see Bendel et al., *Mol. Genetics and Metabolism* 67:343–351, 1999).

However, mortality rates from infections from organisms such as disseminated candidas remain high despite aggressive antifungal therapy (Todischini, *J. Intern Dis.* 1:S37–S41, 1997), and a highly effective method of treating or preventing diseases caused by *Candida albicans* and other similar microorganisms expressing Int1p has yet to be obtained.

SUMMARY OF THE INVENTION

It is thus an object of the present invention to provide a method of effectively treating infection caused by *Candida albicans* and other similar microorganisms which express the Int1p protein.

It is further an object of the present invention to provide a method of effectively treating or preventing infection caused by *Candida albicans*.

It is still further an object of the present invention to provide a method of isolating a propeptide and treating or preventing infection caused by *Candida albicans* through generation of antibodies against the propeptide.

It is even further an object of the present invention to isolate specific regions of the Int1p protein from *C. albicans* and other similar microorganisms such as *S. cerevisiae* which express the Int1p protein, and provide agents and antibodies capable of binding said regions.

It is even further an object of the present invention to isolate specific regions of the Int1p protein from *C. albicans* and other similar microorganisms such as *S. cerevisiae* which express the Int1p protein, and provide peptides or antibodies which can either disrupt the cleaving of the propeptide, or which can act to block the potential binding sites for the propeptide, namely the antigen-presenting cell or the T-lymphocyte binding region.

It is also an object of the present invention to provide a method of inhibiting the activity of the Int1p protein of *Candida albicans* so as to prevent or treat infections caused by microorganisms expressing the Int1p protein.

These and other objections are achieved by the present invention which comprises isolating a peptide from one of a number of specific regions from the Int1p protein of *C. albicans* and treating or preventing an infection from *C. albicans* or other microorganism expressing the Int1p protein by administering to a human or animal patient an effective amount of an antibody composition or other agent which can bind to those specific regions and thus disrupt the activity of the Int1p protein. In particular, the invention relates to the isolation of the propeptide of the Int1p protein and the development of antibodies or other agents which can bind to the propeptide and thus be useful in methods of disrupting the activity of the Int1p protein, such as by preventing the cleaving of the propeptide, and thus prevent or treat infections from *C. albicans* or other microorganisms expressing the Int1p protein. The invention also relates to the generation of peptides which can be used to block the binding of the superantigen to the antigen-presenting cells and/or the T-lymphocytes of the host so as to be useful in methods of preventing or treating infections from *C. albicans* or other microorganisms expressing the Int1p protein

BRIEF DESCRIPTION OF THE DRAWING FIGURES

FIG. 1 is a depiction of the amino acid sequence of the Int1p protein from *C. albicans* (SEQ ID NO:1).

FIGS. 2A and 2B show the nucleic acid sequence coding for the Int1p protein from *C. albicans* (SEQ ID NO:2).

FIG. 5 shows the P Domain subtilisin motifs from a variety of proteins.

FIG. 6 shows a comparison of the high-affinity heparin binding site of *Mycobacterium tuberculosis* heparin-binding hemagglutin adhesin (HBHA) (SEQ ID NO:11) with the heparin-binding site of the Int1p protein of *Candida albicans* (SEQ ID NO:12).

FIG. 9 shows the effects of TSST-1, INT1/INT1 *C. albicans*, int1/int1 *C. albicans*, and phytohemagglutinin on stimulation of Vβ subsets. Unactivated T lymphocytes served as control. *$p<0.05$.

FIG. 10 is a schematic view showing the regions of the Int1p protein, including the catalytic domain (SEQ ID NO:13) and the processing domain (SEQ ID NO:4).

FIG. 11 is a schematic representation of the Int1p peptide regions including an identification of regions recognized by specific rabbit anti-peptide polyclonal antibodies, including the catalytic domains (SEQ ID NO:13) and the processing domain (SEQ ID NO:4).

FIGS. 12A and 12B illustrate the flow cytometry of surface-exposed domains of Int1p when *C. albicans* blastospores are grown to exponential phase in the absence (left panel) or presence (right panel) of 2 units of heparin. X axis represents log-scale fluorescence; Y axis represents percent yeasts fluorescing. Hatched area—fluorescence with anti-INT600. Gray area-fluorescence with anti-CBS2. Fluorescence of *C. albicans* cells incubated with rabbit IgG serves as control-dotted line.

FIGS. 13A, 13B and 13C are Western blots of supernatants from INT1-expressing *S. cerevisiae* grown in the absence or presence of heparin and probed with rabbit polyclonal antibodies to the Int1p amino terminus (anti-INT600), to the second divalent cation binding site (anti-CBS2), or to the RGD domain (anti-RG D).

Figure 14:
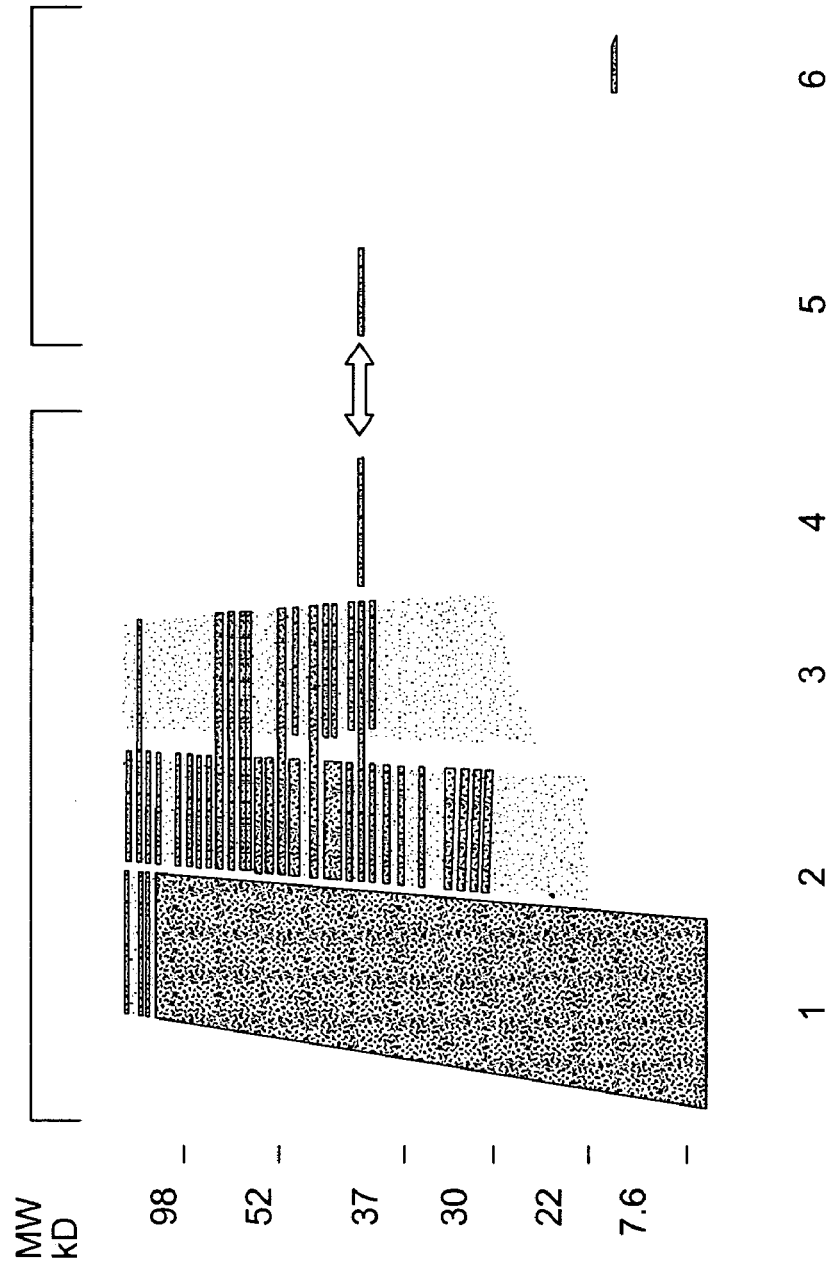

FIG. 14 are immunoblots showing the purification of $Pep_{263}$ Silver stain lanes 1–4. Western blot lanes 5 and 6. Lane 1—*S. cerevisiae* lysate after expression of $Pep_{263}$; lane 2—fraction 300-1 from nickel column; lane 3—fraction 300-2; lane 4—purification of $Pep_{263}$ to homogeneity; Lane 5 shows that a single band of 44 kDa on silver strain (lane 4) reacted with anti-His antibody on Western blot.

Figure 15:
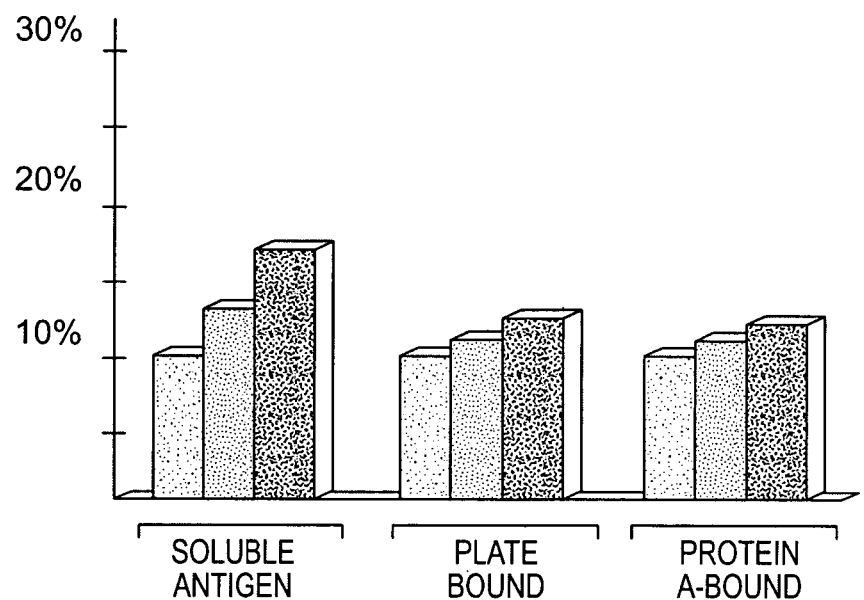

FIG. 15 is a graphic representation of the percent of T lymphocytes up-regulating the IL-2 receptor (Y axis) in response to $Pep_{263}$ presented as soluble antigen (leftmost group of three bars), as antigen bound to the plate (middle group), or as antigen bound to an anti-His antibody attached to protein A beads (right group).

Figure 16:
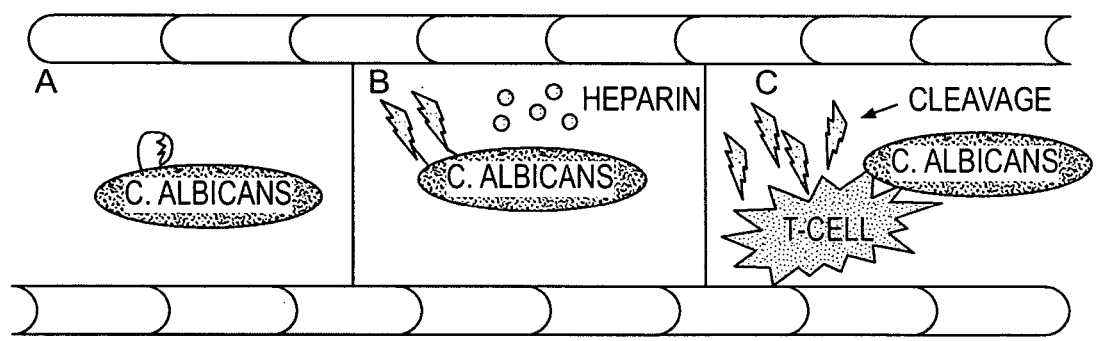

FIG. 16 is a schematic representation of a model for the participation of Int1p in Candidemia.

FIG. 17 shows the MHC-II Binding Sites in the Int1p protein, and in Mycoplasma arthritidis, as disclosed in *J. Exp. Med.* 183:1105–1110 (1996), incorporated herein by reference. This figure includes FVQNL (SEQ ID NO:5), NNVVFTNKELE (SEQ ID NO:6), FAQLLNKNNEV (SEQ ID NO:7) and NSEPE (SEQ ID NO:8)

Figure 18:
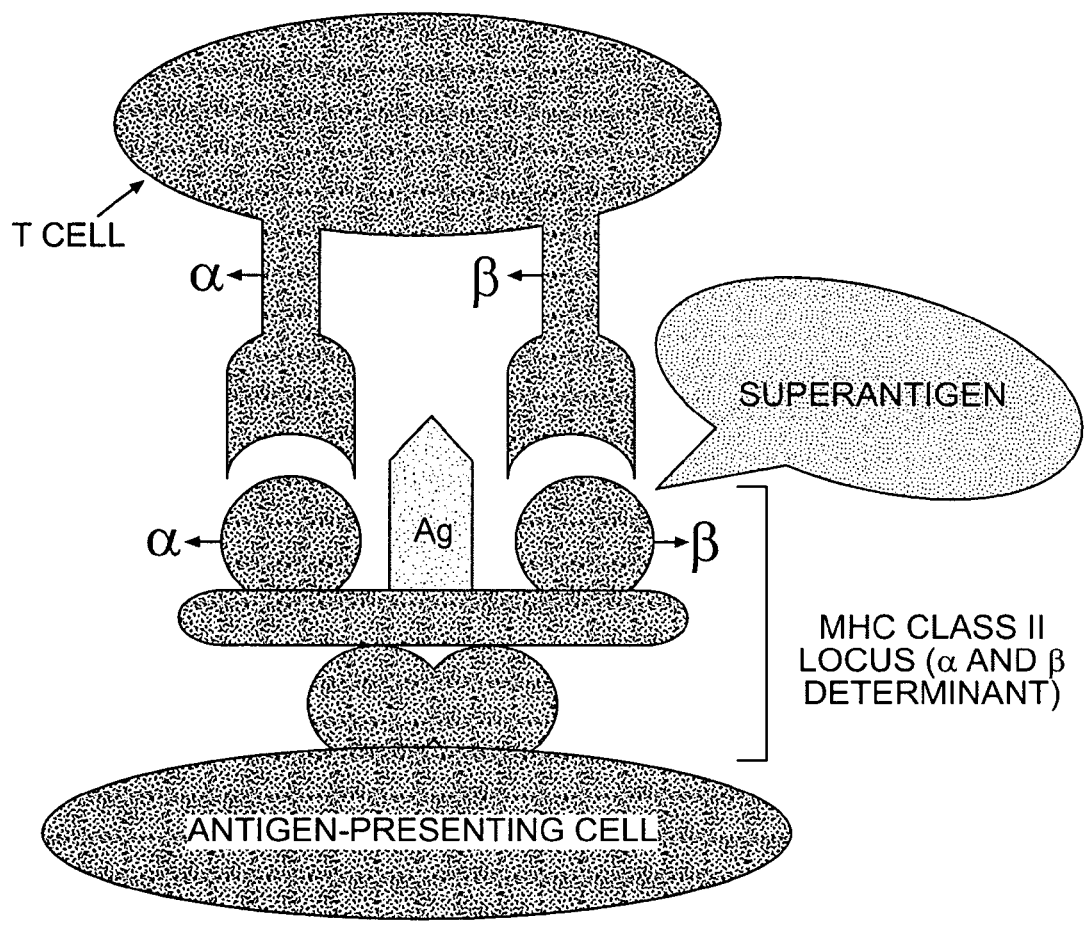

FIG. 18 shows the linkage of the T lymphocyte to the antigen-presenting cell through the superantigen which is produced after the propeptide is cleaved.

DETAILED DESCRIPTION OF THE PREFERRED EMBODIMENTS

In accordance with the present invention, the present inventors have now discovered and isolated several distinct regions of the Int1p protein, and the present invention is directed to treating or preventing infections from microorganisms which express the Int1p protein, including yeast of the *Candida* species such as *Candida albicans*, and other microorganisms such as *S. cerevisiae*, by disrupting the regions, including the propeptide region, which are involved with the pathways by which the Int1p protein is activated in a host. In addition, the present invention is directed to agents and antibodies which can bind to the specific regions of the Int1p protein and which thus can be useful in treating or preventing *C. albicans* infections. In general, it is desired to develop antibodies which can prevent the propeptide from cleaving, and/or antibodies that will bind to the propeptide and thus disrupt the activation of the Int1p protein.

In one of the preferred embodiments of the invention, the invention relates to peptides, either linear or cyclic, which have the same sequence as that of the sites on the superantigen propeptide which will bind to two sites, namely the antigen-presenting cell (such as the MHC-II locus) and the T lymphocytes on the host cell. In the Int1p protein, the MHC-II binding peptide appears to be in the region of from amino acid 239 through 254 (in the propeptide region of 1–263) of the sequence of the protein shown in FIG. 1 and this sequence is shown in FIG. 17. Accordingly, the use of this peptide, or other blocking peptides, is contemplated in accordance with the invention in any suitable form, e.g., pharmaceutically acceptable compositions, as would be used for administration to a human or animal patient. These types of blocking peptides can thus be administered to the host as a method of blocking the sites that would become bound to the superantigen propeptide, and thus can be used to prevent or treat infections caused by the Int1p protein.

In a further aspect of the present invention, it is contemplated that treatment or prevention of infections caused by microorganisms such as *C. albicans* may be achieved by causing mutations in the specific regions as set forth herein which can cause conformational or other changes to the peptides coded by these regions and thus disrupt the immunomodulatory ability of the Int1p protein. The gene sequence and the peptide sequence for the Int1p protein has previously been disclosed, e.g., in *Proc. Natl. Acad. Sci. U.S.A.* 93 (1), 357–361 (1996), incorporated herein by reference. In addition, further information regarding Int1p has been provided in pending U.S. patent application Ser. No. 09/264,604 and in U.S. Pat. No. 5,886,151, both incorporated herein by reference. Finally, the amino acid sequence of the Int1p protein is shown in FIG. 1, and the DNA sequence is shown in FIGS. 2a–2b. In the preferred embodiments, those mutations in accordance with the invention will be those which can prevent the cleaving of the propeptide, or which can disrupt the binding of the propeptide superantigen to the antigen-presenting cells or to the T lymphocytes of the host. Accordingly, in accordance with the invention, mutations in either or both of these propeptide binding regions are preferred.

As will be shown further below, the present invention thus relates to antibodies which can bind to the specific regions from the *C. albicans* Int1p protein as set forth below and the use of those antibodies in disrupting the *C. albicans* activity in human or animal hosts so as to prevent or treat infections caused by this or other similar microorganisms expressing the Int1p organism. Accordingly, in one embodiment, the present invention relates to isolated and/or purified antibodies, such as polyclonal or monoclonal antibodies, which have been generated against specific regions of the *C. albicans* Int1p protein which can be useful in methods of preventing and treating candidal and other yeast infections caused at least in part by the Int1p protein and its immunomodulatory ability. The term "antibodies" as used herein includes monoclonal, polyclonal, chimeric, single chain, bispecific, simianized, and humanized or primatized antibodies as well as Fab fragments, including the products of an Fab immunoglobulin expression library, and generation of any of these types of antibodies or antibody fragments is well known to those skilled in the art. As indicated above, it is desirable to provide antibodies which can disrupt the activation of the Int1p protein in any of a number of ways, including preventing the cleaving of the propeptide, or disrupting the binding of the cleaved superantigen to host cells at its binding sites, namely the antigen-presenting cell (such as the MHC-II locus) or the superantigen-binding site on T lymphocytes. As described further below, these antibodies are preferably used in amounts effective to prevent or treat infections from *C. albicans* and other similar microorganisms, and these antibodies may be produced in any of a number of suitable ways well known in the field to produce polyclonal or monoclonal antibodies. For example, in addition to generating polyclonal antibodies by injecting the isolated peptides of the invention into a suitable animal model and isolating the antibodies therefrom, monoclonal antibodies directed to the Int1p regions described below may also be generated using the method of Kohler and Milstein (see, e.g., *Nature* 256:495–7, 1975), or other suitable ways known in the field. Antisera prepared using monoclonal or polyclonal antibodies in accordance with the invention are also contemplated and may be prepared in a number of suitable ways as would be recognized by one skilled in the art.

In addition, the invention relates to the use of agents which can bind to the specific regions below so as to disrupt these peptides and again inactivate the infectious and immunomodulatory pathways by which microorganisms expressing the Int1p protein by become virulent. Finally, it is also contemplated that mutations to these regions, whether to the amino acid sequences or to the nucleic acid sequences coding these peptides, may also be utilized in order to disrupt the functioning of the Int1p protein and to make the infectious microorganisms ineffective or less virulent.

In one embodiment of the present invention, the invention relates to the isolation of the propeptide of the Int1p protein and the use of this propeptide in generating antibodies and other agents which will be useful in the treatment or prevention of *C. albicans* infection. This propeptide constitutes amino acids 1–263 of the Int1p protein, such as shown in FIG. 1, and has been identified as peptide $Pep_{263}$. As the present inventors have determined, the propeptide, $Pep_{263}$ constitutes a superantigen-like moiety which is released from Int1p and which plays a major role in activating T lymphocytes in host cells. Accordingly, an antibody or other agent capable of binding to this propeptide can be utilized in a method of disrupting the activation of T lymphocytes caused by microorganisms such as *C. albicans* and *S. cerevisiae*, and thus can be utilized in methods of preventing, treating, or reducing the virulence of infections from such microorganisms which express Int1p. In particular, the antibody to the propeptide in accordance with the present invention will be able to disrupt the functioning of the Int1p protein, e.g., such as by binding the propeptide and/or preventing the cleaving of the propeptide and thus stopping the release of the propeptide in its superantigen form.

The propeptide $Pep_{263}$ also contains a heparin binding site at amino acids 155–169, and it appears that activation of T lymphocytes is triggered by $Pep_{263}$ when this peptide is cleaved from the amino terminus of Int1p in a reaction accelerated by physiologic doses of heparin. In the absence of heparin, $Pep_{263}$ appears to be covert and is generally not detectable by antibodies such as anti-INT600, an antibody to the first 600 amino acids of the Int1p protein. However, in the presence of heparin, the amino terminus of Int1p is exposed, at which point $Pep_{263}$ is cleaved and released into the fluid phase where it exhibits superantigen-like effects culminating in the release of pro-inflammatory cytokines that influence the clinical outcome and cause or enhance infection of microorganisms such as *C. albicans* and *S. cerevisiae* which express Int1p. Accordingly, agents and antibodies to $Pep_{263}$ in accordance with the present invention can be useful in methods to prevent or treat infections in microorganisms expressing the Int1p protein and to eliminate or reduce the activation of T lymphocytes caused therefrom.

Figure 3:
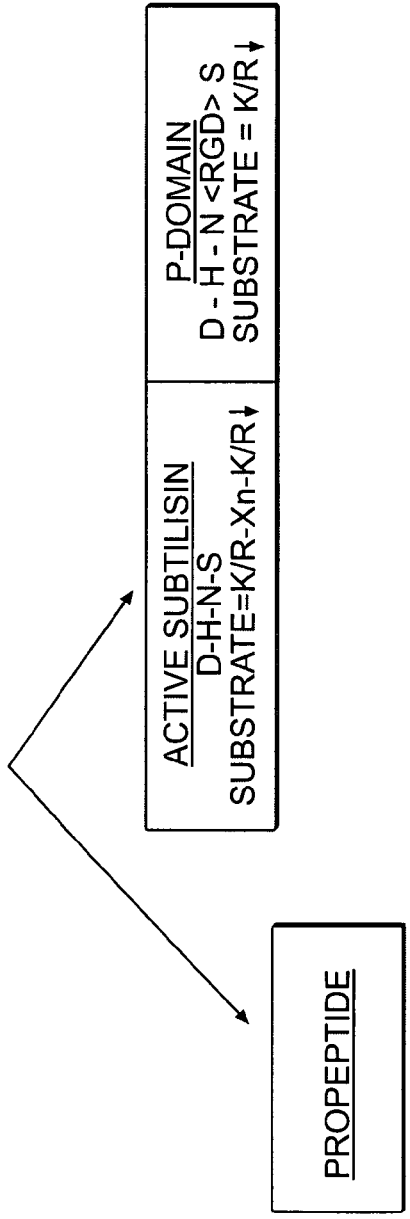
FIG. 3 is a schematic representation of the activation of a general proprotein convertase which shows the presence of a signal peptide, the propeptide, an inactive subtilisin and P-domain, and the manner of activation. This figure includes DHNS (SEQ ID NO:3) and DHNRGDS (SEQ ID NO:4)
Figure 4:
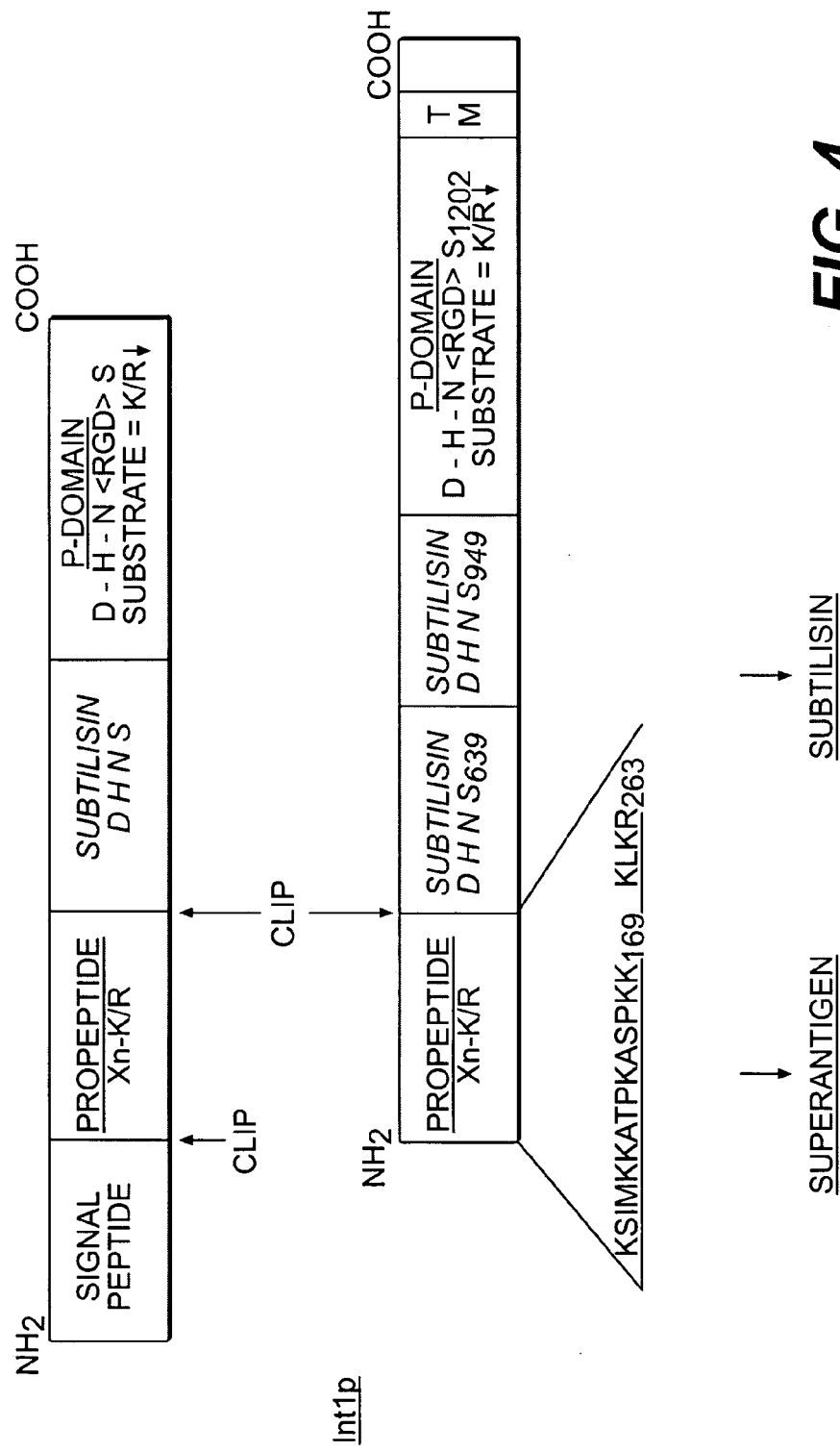
FIG. 4 is a schematic representation of the intip protein as compared to a generic proprotein convertase which illustrates the clipping of the Int1p propeptide which is cleaved to become a superantigen at the same time the subtilisin regions are activated as well. This figure includes DHNS (SEQ ID NO:3) and DHNRGDS (SEQ ID NO:4)

As shown in the schematic drawing FIGS. 3 and 4, activation of "subtilisin-like" proprotein convertases occurs in the Int1p protein which ultimately leads to the cleaving of the propeptide and the activation of the virulent form of the microorganism. In FIG. 3, the schematic analysis of the Intip protein shows the presence of a signal peptide, the propeptide, an inactive subtilisin and the P-domain. The processing or "P-domain" is employed to clip the propeptide at the carboxy terminal side of dibasic residues, thereby releasing the propeptide. Exposed D-H-N-S (SEQ ID NO:3) active site residues assume the subtilisin serine protease conformation. This amino terminal processing is shown further in FIG. 4 wherein the original form of Int1p is transformed by the clipping of the propeptide, which includes heparin binding region 155–169, and which is cleaved to become a superantigen at the same time the subtilisin regions are activated as well. P Domain subtilisin motifs from a variety of proteins are compared as shown in FIG. 5. FIG. 6 shows a comparison of the high-affinity heparin binding site of Mycobacterium tuberculosis heparin-binding hemagglutin adhesin (HBHA) with the heparin-binding site of the Int1p protein of *Candida albicans*.

As thus has been shown by the present inventors, the specific regions of the Int1p protein which are involved in the activation of T lymphocytes by this protein all present target sites for disruption of infectivity and virulence of microorganisms that express this protein such as *C. albicans* and *S. cerevisiae*. As indicated above, the propeptide region at amino acids 1–263 which includes a heparin binding site is critical to the activation process in that this propeptide is cleaved from the protein in order to become a superantigen which has been shown to be able to immunomodulate host cells. In accordance with the invention, antibodies or other agents which can bind this region can thus be useful to prevent T-cell activation and can thus be employed in methods of preventing or treating outbreaks of infections from microorganisms expressing Int1p.

Still other specific regions utilized in the activation process have been identified, and these peptides can be isolated and/or purified so as to be used in generating antibodies and other agents which will bind to these proteins or otherwise be able to disrupt the Int1p activation process. Included in these regions in addition to the propeptide region at amino acids 1–263 are the Catalytic domain 1 at amino acids 435–639, the Catalytic domain 2 at amino acids 738–949, and the Processing domain (or "P-domain") motif at amino acids 1022–1236, as best shown in FIG. 11. In accordance with the present invention, isolated and/or purified antibodies, produced for example in the manner described above, may be generated against the specific regions recited above, and effective amounts of said antibodies may be employed in methods of preventing or treating infections from *C. albicans* or other microorganisms that express the Int1p protein. Similarly, other methods of treatment or prevention in accordance with the present invention would include agents which bind to or otherwise disrupt these specific regions so as to reduce or eliminate Int1p activity, or mutations in these specific regions of wild-type sequences which also are effective in reducing or eliminating Int1p activity. As indicated above, in the most desirable embodiment, these antibodies will function so as to disrupt Int1p activity, such as by binding the peptide regions and/or preventing the cleaving of the propeptide and thus stopping the release of the propeptide in its superantigen form.

In addition, other peptides or antibodies which can disrupt the binding of the superantigen to the host cells are also provided in accordance with the invention. The superantigen enables the activation of T lymphocytes through a two-fold binding system wherein the superantigen binds to both the T cell and to the antigen-presenting cell, such as at the MHC Class II locus, such as shown in FIG. 18.

It is also contemplated that isolated nucleic acids coding for the regions set forth above, namely the propeptide region at amino acids 1–263, the catalytic domains 1 and 2, and the processing domain as shown in FIG. 11, will be contemplated in accordance with the present invention. As would be recognized by one skilled in the art, nucleic acid sequences in accordance with the invention will include not only the specific regions of the nucleic acid sequence as shown in FIGS. 2A–2B which correspond to the peptide regions as set forth above, but to any alternative nucleic acid sequences coding for those amino acid sequences. The isolated nucleic acids of the invention will be useful in many appropriate ways, including generating the peptide regions in accordance with the invention through recombinant means so that these recombinant peptides may be used to generate appropriate antibodies. In addition, it is contemplated that mutations to the peptide and nucleic acid sequences in these regions will also be useful in providing alternative methods by which to disrupt the Int1p activation pathways.

In addition to the use of agents and antibodies which bind to the propeptide and/or other specific regions of the Int1p protein as set forth above in methods of treating or preventing infection, the present invention also contemplates the use of these antibodies in a variety of ways, including the detection of the presence of microorganisms such as *C. albicans* or *S. cerevisiae* and thus using antibodies to diagnose infections caused by microorganisms expressing Int1p, whether in a patient or in medical materials which may also become infected, is contemplated in accordance with the invention. For example, one such method of detecting the presence of infections by microorganisms expressing Int1p involves the steps of obtaining a sample suspected of being infected, and lysing the cells so that the DNA can be extracted, precipitated and amplified. Following isolation of the sample, diagnostic assays utilizing the antibodies of the present invention may be carried out to detect the present of Int1p microorganisms such as *C. albicans* or *S. cerevisiae*, and such assay techniques for determining such presence in a sample are well known to those skilled in the art and include methods such as radioimmunoasssay, Western blot analysis and ELISA assays.

Accordingly, antibodies in accordance with the invention may be used for the specific detection of Int1p-producing microorganisms, for the prevention or treatment of infection from said microorganisms, or for use as research tools. As indicated above, the term "antibodies" as used herein includes monoclonal, polyclonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art.

As would also be recognized by one skilled in the art, the antibodies of the present invention may also be formed into suitable pharmaceutical compositions for administration to a human or animal patient in order to treat or prevent an infection caused by yeast such as *C. albicans* or *S. cerevisiae*. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops or solution. Alternatively, when so desired, wound or surgical dressings, sutures and aerosols may be impregnated with the composition to further prevent infection. The composition may contain conventional additives, such as preservatives, solvents to promote penetration, and emollients. Topical formulations may also contain conventional carriers such as cream or ointment bases, ethanol, or oleyl alcohol.

Still further, the isolated antibodies of the present invention, or active fragments or portions as set forth above, may also be utilized in the development of vaccines for passive or active immunization against candidal-type infections or other infections associated with Int1p-producing microorganisms. Further, these compositions may also be administered to a wound or used to coat medical devices or polymeric biomaterials in vitro and in vivo. In addition, the antibody may be modified as necessary so that, in certain instances, it is less immunogenic in the patient to whom it is administered. For example, if the patient is a human, the antibody may be "humanized" by transplanting the complimentary determining regions of the hybridoma-derived antibody into a human monoclonal antibody as described, e.g., by Jones et al., Nature 321:522–525 (1986) or Tempest et al. Biotechnology 9:266–273 (1991).

In one embodiment, the isolated peptides in accordance with the invention may be used in the preparation of a vaccine which comprises one or more of the Int1p peptides as described above in an amount sufficient to generate an immunological response. In addition, antibodies in accordance with the invention may be used as a passive vaccine which will be useful in providing suitable antibodies to treat or prevent candidal or other similar infections. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. Although many methods of administering the vaccine will be suitable, the particular mode of administration will depend on the nature of the infection to be dealt with and the condition of the patient. The vaccine is preferably combined with a pharmaceutically acceptable carrier to facilitate administration, and the carrier may be include common materials such as water or a buffered saline, with or without a preservative. The vaccine may be lyophilized for resuspension at the time of administration or in solution.

The preferred dose for administration of an antibody composition in accordance with the present invention is that amount will be effective in preventing of treating a yeast infection or infection from other microorganisms that express the Int1p protein. As one skilled in the art would recognize, such an effective amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. The exact amount of the antibody or a particular agent that is required will thus vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances. However, an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma. Chemical Company, St. Louis, Mo.).

In another embodiment of the present invention, a kit which may be useful in isolating and identifying infections caused by microorganisms expressing Int1p which comprises the antibodies of the present invention in a suitable form, such as lyophilized in a single vessel which then becomes active by addition of an aqueous sample suspected of being infected with C. albicans or other similar microorganism. Such a kit will typically include a suitable container for housing the antibodies in a suitable form along with a suitable immunodetection reagent which will allow identification of complexes binding to the specific regions of the Int1p protein as set forth above. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen. Additionally, a method of identifying or diagnosing an infection of C. albicans or other microorganism expressing the Int1p protein is also provided wherein one or more antibodies to the peptide regions set forth above from the Int1p protein are introduced into a sample thought to be infected with a microorganism expressing Int1p, and the identification or diagnosis of the infection can be confirmed if binding to the sample is observed. Such binding can be observed in any of a number of suitable ways commonly used in the art, including, e.g., detectable labels, as described above.

In summary, the present invention thus provides isolated and/or purified regions of the Int1p protein which have been shown to be involved in pathways of activation which results in the virulent spread of microorganisms expressing Int1p, and also provides antibodies, antisera, and other agents which can bind to these specific regions, and/or which can disrupt the process of Int1p activation in other ways. Such antibodies and agents can therefore be utilized in effective methods of treating or preventing infections from microorganisms such as C. albicans or S. cerevisiae which express the Int1p protein.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Investigations of the Int1p Protein

The protein Int1p of *Candida albicans* functions as an adhesin, participates in morphologic switching of blastospores to hyphae, and is linked to virulence in mice. Rapid mortality ascribable to INT1/INT1 strains suggested that Int1p may have an immunomodulatory role. Therefore, we investigated whether expression of Int1p on the surface of *C. albicans* influenced T cell activation.

*C. albicans* strains used in the Investigations:

| | | | |
|---|---|---|---|
| CAF2 | INT1/INT1 | URA3/ura3 | |
| (supplied by W A Fonzi, Georgetown University, Washington D.C.) | | | |
| CAG1 | INT1/int1 | URA3/ura3 | |
| (see Gale et al., Science 279:1355–1358, 1998) | | | |
| CAG3 | int1/int1 | URA3/ura3 | |
| (see Gale et al., Science 279:1355–1358, 1998) | | | |
| HLC-54 | INT1/INT1 | URA3/ura3 | cph1/cph1 efg1/efg1 |
| (supplied by J R Kohler, Whitehead Institute, MIT, Cambridge, MA). | | | |

Culture Conditions:

Blastospores grown to mid-exponential phase in YPD medium at 30° C. shaking, were washed in PBS containing the subinhibitory dose of 0.2 μg/ml amphotericin B (Al-Bassam et al., *J. Antimicrob Chemother,* 15:263–269, 1985). Yeast were adhered to the bottom of 96 well culture plates by incubating 500,000 cells/well for 45 minutes at 37° C.

Peripheral blood mononuclear cells (PBMC) were obtained by Ficoll-hypaque centrifugation of heparinized blood. Washed PBMCs were suspended in RPMI1640 supplemented with 10% human AB serum, L-glutamine, sodium pyruvate, nonessential amino acids and 0.2 μg/ml amphotericin B to maintain *Candida albicans* in the blastospores stage.

Cocultures were initiated by adding 200λ PBMCs at $2.5 \times 10^6$ cells/ml to the adherent blastospores upon removal of PBS/amphotericin B. Cultures were incubated at 37° C. 5% $CO_2$ for 1–7 days. Control wells containing PBMC±superantigen TSST-1 and the mitogen PHA were also established. The effect of MHC class II inhibition was assessed by adding anti-HLA-DR antibody to PBMCs prior to coculture. Where appropriate, CD3 cells were isolated to >97% purity using cell separation columns. Antigen presenting cells (APC) expressing MHC class II were isolated by plastic adherence. The antigen processing ability of APCs was abolished by pretreatment with 0.3% paraformaldehyde.

Flow Cytometry:

Cultures harvested at appropriate time points were stained for 10 minutes at RT with PE and FITC conjugated monoclonal antibodies to IL2R and CD3, respectively, to assess T cell activation. Similarly, T cell subsets CD4 and CD8 as well as $V_{beta}2$ and $V_{beta}8$ were analyzed by using Cychrome and PE labelled Mabs, respectively. Cells were quantitated by flow cytometry using FACS Vantage. (BD Biosciences, San Jose, Calif.) Data analysis was performed using WinMD1 version 2.8 software. (Kindly supplied by Dr. Joseph Trotter, Scripps Research Institute, LaJolla, Calif.)

Methods:

PBMCs from five normal healthy volunteers were cocultured with either CAF2 INT1/INT1 or CAG3 int1/int1 blastospores for days 1 through 7. IL2 receptor positive cells among the CD3 positive population indicate the frequency of activated T cells at each time point. Tests on five individuals showed that by day 4, the frequency of activated T cells was significantly greater for CAF2 cocultures. Clusters of activated T cells were also predominant by day 4 of PBMCs cocultured with INT1/INT1 blastospores. Under similar experimental conditions, int1/int1 blastospores do not induce these T cell activation clusters.

PBMCs from a single donor were cultured alone or with *C. albicans* strains CAF2, CAG1, CAG3 or HLC-54 for five days. Only strain CAG3, the int1/int1 null mutant failed to activate T cells above the level of unstimulated control.

PBMCs were cultured with either 10 μg/ml PHA, 4μg/ml TSST-1 or 500,000 blastospores of either CAF2 or CAG3. Each culture condition was either left untreated or incubated with 10 μg/ml of either anti-HLA-DR antibody or an isotype control. CD3 positive cells were analyzed for IL2 receptor upregulation by flow cytometry. T cell activation induced by PHA was unaffected by anti-HLA-DR antibody as anticipated since mitogen activation is independent of MHC class II. However, the response to superantigen TSST-1 was significantly inhibited since binding to $V_{beta}2$ of the TCR and the beta chain of class II is required for activation. Anti-HLA-DR antibody significantly depressed the upregulation of IL2R on T cells cocultured with CAF2 INT1/INT1 but not with CAG3 int1/int1 suggesting a role for MHC class II molecules in Int1p-mediated T cell activation.

Cultures as described above were expanded during the last 24 hours of culture with human IL2. Cultures were analyzed by flow cytometry for the expansion of either T cell $V_{beta}2$ or $V_{beta}8$ subsets. Significant expansion of the $V_{beta}2$ subset occurred in activations with the $V_{beta}2$ specific superantigen TSST-1 as well as with blastospores of CAF2 but not with CAG3. The frequency of $V_{beta}8$ T cells was similar to the unactivated control for all conditions. Thus, there is preferential expansion of at least the $V_{beta}2$ subset by *C. albicans* expressing Int1p.

PBMCs that were cocultured with either CAF2 INT1/INT1 or CAG3 int1/int1 blastospores were tested to determine frequencies of CD4 and CD8 T cells by flow cytometry. The ratio of CD4:CD8 cells was <1:1 for T cells expanded by CAF2 INT1/INT1, whereas all other activation conditions had ratios >1:1. CAF2 modulation of the CD4:CD8 ratio which was evident in the $V_{beta}2$ T cell subset of one of the donors evidences a role for Int1p in activation-induced CD4 T cell loss.

T cells ($2.5 \times 10^5$) were cultured with either 500,000 CAF2 blastospores or 4 μg/ml TSST-1 in the presence of APC ($2.5 \times 10^5$) pretreated with or without 0.3% paraformaldehyde. In this case, T cell activation by CAF2 INT1/INT1 blastospores occurred despite the inability of MHC class II expressing APCs to process antigen. Similarly, activation by TSST-1 was not inhibited by paraformaldehyde fixation of APC.

In summary, equal numbers of *C. albicans* blastospores from strains CAF2 INT1/INT1 and CAG3 int1/int1 in mid-exponential phase were incubated with PBMCs isolated from 5 normal healthy volunteers. IL2 receptor upregulation on CD3 cells was monitored by flow cytometry. The percentage of CD3 cells expressing IL2 receptor was significantly greater for activations using CAF2 blastospores (42.0+/−6.3) than for CAG3 (3.8+/−1.0), p=0.005. Antibodies to HLA-DR inhibited IL2 receptor expression on T cells activated by CAF2, but had no effect on T cells activated by CAG3. Preliminary data indicated a preference for $V_{beta}2$ T cell activation by CAF2. Analysis of CD4:CD8 subsets revealed that T cells activated by CAG3 blastospores had a normal CD4:CD8 ratio (2:1) similar to control T cells expanded with human IL2. However, after incubation with Int1p-expressing CAF2 blastospores, the CD4:CD8 ratio was depressed (<1:1) due to a reduction in the number of CD4 T cells. Thus, activation of a specific $V_{beta}$ subset of T lymphocytes and depletion of CD4 cells are two mechanisms by which Int1p-bearing *C. albicans* modulate the cell-mediated immune response.

As a result of the above experiments, the following conclusions can be drawn:

*Candida albicans* blastospores expressing the protein Int1p activate human T lymphocytes whereas blastospores lacking Int1p surface expression do not.

Inhibition of IL2 receptor upregulation by anti-HLA-DR antibody indicates a dependence for MHC class II in Int1p induced T cell activation.

T cell activation by Int1p expressing blastospores is independent of antigen processing as indicated by resistance to APC paraformaldehyde fixation.

*Candida albicans* expressing Int1p preferentially activate the $V_{beta}2$ T cell subset.

Activation induced deletion of CD4 T cells by Int1p is a mechanism by which *Candida albicans* can modify the host immune response.

Example 2

Additional Investigations of the Int1p Protein and the Isolation of the Propeptide from *Candida Albicans*

INT1 Gene in *Candida albicans* and its Importance in Pathogenesis

Some years ago, we identified the *Candida albicans* gene INT1, which encodes a protein of Mr 188 kDa that mediates adhesion, medium-dependent filamentation, and virulence. See, e.g., Gale et al. *PNAS* 93:357–61 (1996); Gale et al. *Science* 279:1355–58 (1998), incorporated herein by reference. In particular, ICR mice given a tail vein injection of $10^5$ wild type *C. albicans* expressing both INT1 alleles (genotype INT1/INT1) showed 100% mortality by day eleven, while 90% of mice given a homozygous double disruptant (genotype INT1/int1) survived. Animals given a heterozygous mutant (genotype INT1/int1) or a re-integrant (genotype int1/int1/INT1) had intermediate mortality (40% survival). All strains replicated equally well and underwent filamentous growth in serum, and no differences in CFU in blood, kidney, or liver were found (36). Thus, defects in replication, filamentation, or organ dissemination did not explain INT1-dependent mortality.

INT1-Expressing *C. albicans* Activate T Lymphocytes, but the int1 Knockout Strain Does Not We therefore asked, "Why is the presence of INT1 associated with death in mice?" Unlike other fungi, *C. albicans* does not produce mycotoxins, but based on the available evidence, we considered the possibility that the encoded protein Int1p, or some part of it, might be a superantigen.

Figure 7:
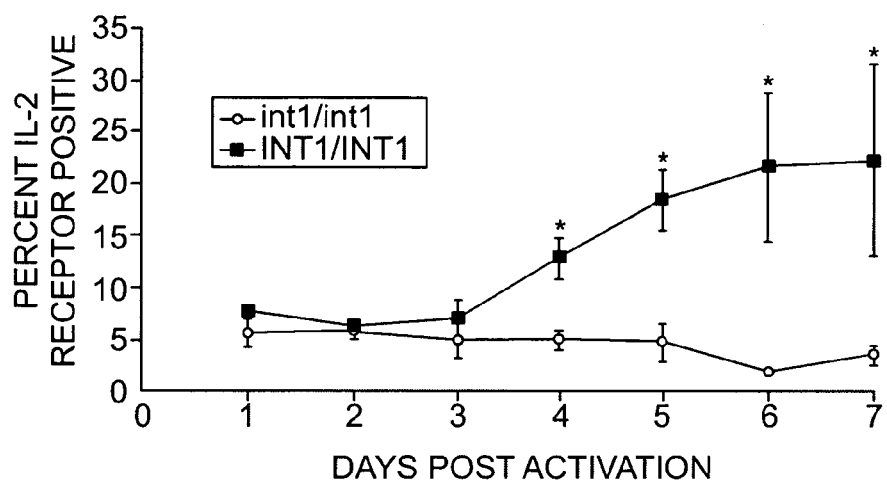
FIG. 7 depicts the activation of T lymphocytes after incubation with INT1/INT1 blastospores (squares) or int1/int1 blastospores (diamonds). Data from five normal adult donors are shown. *$p<0.05$.

Peripheral blood mononuclear cells (PBMC's) from five normal donors were obtained by Ficoll-Hypaque centrifugation, suspended in RPMI 1640 supplemented with 10% human AB serum, L-glutamine, sodium pyruvate, non-essential amino acids, and 0.2 µg/ml amphotericin B to prevent germ tube formation. See FIG. 7. PBMC's were incubated at 37° C. in 5% $CO_2$ with $10^5$ blastospores of INT1/INT1 *C. albicans* or an equal number of int1/int1 *C. albicans* (homozygous double disruptant) for one to seven days (n=7 expts.) The superantigen TSST-1 (800 µg/well) or the mitrogen PHA served as controls. Two color flow cytometry was used to plot the percentage of CD3 positive cells that expressed the IL-2 receptor (CD25).

Results: Although no significant activation of T lymphocytes was observed for the first three days of culture, on days four through seven, PBMC's incubated with INT1/INT1 *C. albicans* showed a significant increase in expression of the IL-2 receptor (CD25) on CD3+ cells, a marker for lymphocyte activation. PBMC's form the same donors did not increase expression of the IL-2 receptor when incubated with the int1/int1 double disruptant. These results indicate that Int1p is required for activation of T lymphocytes by *C. albicans*.

Activated T lymphocytes were predominantly of the CD4 subset and were eliminated within 7–10 days after co-culture. In all donors, the CD4/CD8 ratio, which ranged from 1.8:1 to 2.2:1 on day 3, was reversed by day 7.

Figure 8:
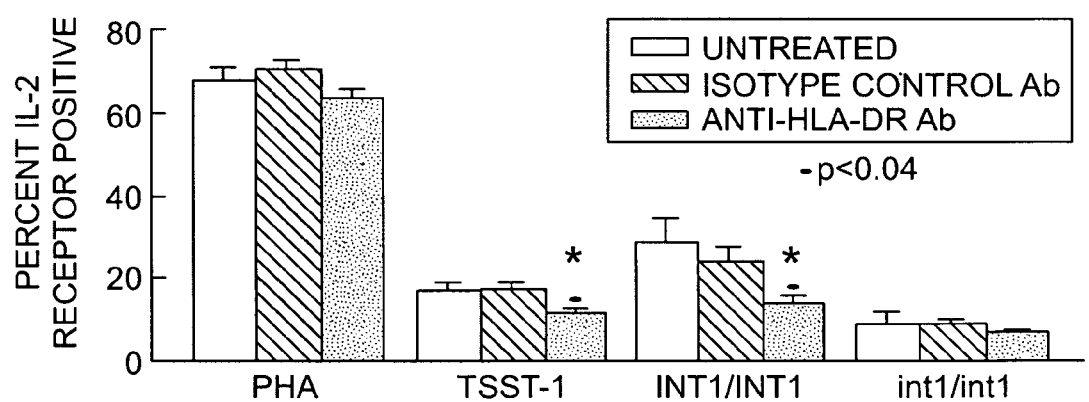
FIG. 8 depicts the effects of antibodies against the MHC Class II determinant HLA-DR (black columns) on lymphocyte activation in response to PHA, TSST-1, INT1/INT1 *C. albicans*, or int1/int1 *C. albicans*. An irrelevant murine IgG (hatched bars) served as isotype control. *$p<0.04$.

INT1-Associated Activation of T Lymphocytes can be Blocked by Antibodies to MHC Class II PBMC's were pre-incubated with a monoclonal antibody to HLA-DR prior to stimulation with the mitogen PHA, the superantigen TSST-1, INT1/INT1 *C. albicans*, or int1/int1 *C. albicans*. T cell activation (up-regulation of the IL-2 receptor CD25) was measured by two-color flow cytometry and plotted on the Y-axis. See FIG. 8.

Results: Antibodies against MHC Class II HLA-DR significantly inhibited T lymphocyte activation induced by toxic shock toxin TSST-1 and INT1/INT1 *C. albicans*. Anti-HLA-DR antibodies did not block T lymphocyte-activation induced by the T cell mitogen PHA (which does not require antigen-presenting cells for its effects) or by int1/int1 *C. albicans*. These results confirm the participation of MHC Class II in the activation response of T lymphocytes stimulated by TSST-1 or INT1/INT1 *C. albicans*.

T Lymphocyte Activation in Response to Int1p Does Not Require Antigen Processing or Presentation by Antigen-Presenting Cells (APC's)

APC's were separated from PBMC's by a glass wool column and pre-treated with 0.3% paraformaldehyde (PFA) before being returned to co-culture with lymphocytes. TSST-1 and INT1/INT1 *C. albicans* were used as stimuli. In the absence of PFA, 44% of T lymphocytes were activated with INT1/INT1 *C. albicans* as stimulus; in the presence of PFA, 43% were activated. With TSST-1 as stimulus, 60% of T lymphocytes were activated in the absence of PFA treatment of APC's; in the presence of PFA, 56% were activated. Thus, PFA treatment did not inhibit T lymphocyte activatien in response to TSST-1 or to INT1/INT1 *C. albicans*. When leupeptin and pepstatin were used to inhibit antigen processing and presentation, respectively, lymphocyte activation in response to TSST-1 and INT1/INT1 *C. albicans* was not inhibited. These results show that lymphocyte activation by Int1p is independent of antigen processing and presentation by APC's.

Expansion of Identical Vβ Subsets by the Soluble Superantigen TSST-1 and Int1p

The expansion of Vβ subsets was measured after stimulation of PBMC's with TSST-1 (800 μg), with INT1/INT1 *C. albicans*, with int1/int1 *C. albicans*, and with PHA. Unactivated PBMC's served as control (FIG. 9).

Results: Incubation of PBMC's with wild type *C. albicans* (INT1/INT1) or TSST-1 preferentially expanded the Vβ2 subset of T-lymphocytes (black bars) but not the Vβ8 subset (open bars). There was no significant expansion of the Vβ2 subset when lymphocytes were incubated with int1/int1 *C. albicans* (double disruptant) or with phytohemagglutin. These preliminary experiments show Vβ subset specificity in response to TSST-1 and Int1p: comparing INT1+ strains and int1− strains confirms that expansion of the Vβ2 subset was INT1-dependent.

Release of Pro-Inflammatory Cytokines

Peripheral blood mononuclear cells were stimulated with $5 \times 10^5$ INT1/INT1 *C. albicans* blastospores, and production of TNFα, IL-6 and IL-4 was measured in supernatants on days 2, 4 and 6. As can be seen from the table below, INT1/INT1 *C. albicans* induce a predominantly Th1 response in vitro with elevations in TNFα and IL-6 that are comparable to those induced by staphylococcal enterotoxin B (SEB), a well-characterized superantigen. There is virtually no production of IL-4 in response to *C. albicans* or SEB. Interestingly, the TNFα response to *C. albicans* showed a near 40-fold variance (high responder=7014 pg/ml on day 2; low responder=165 pg/ml on day 2), while the response to SEB did not differ significantly in these two donors. Although one reason for the more consistent response to SE could be its use as a soluble protein, another possible interpretation is that the response to *C. albicans* involves different MHC Class II alleles, different Vβ subsets, or differing kinetics of T cell activation and apoptosis. Hypothesis Two will address this possibility.

preferentially expanded by *S. cerevisiae* expressing INT1; no expansion of Vβ2 or Vβ8 subsets was noted in response to *S. cerevisiae* transformed with vector alone.

| EFFECTS of Int1p PROTEIN in *C. ALBICANS* or *S. CEREVISIAE* | |
|---|---|
| X | Activates T lymphocytes, up-regulates IL-2 receptor, and releases pro-inflammatory cytokines |
| X | Requires antigen-presenting cells (APC's) for co-stimulatory molecules but not for antigen presentation or processing |
| X | Expands particular Vβ subsets |

These experiments indicated that the presence of the protein Int1p was associated with superantigen-like effects, both in wild type *C. albicans* and in transformed *S. cerevisiae*. These are imperfect experiments because they compare a soluble superantigen (TSST-1) with either INT1+ or int1− strains of *C. albicans*; nevertheless, the results provide some indication that superantigen-like effects were associated with INT1+ *C. albicans*. However, because most superantigens are secreted proteins of 22–29 kDa, and Int1p has a predicted mass of 188 kDa in its unglycosylated form, we hypothesized that limited proteolysis of Int1p might generate a soluble polypeptide that could serve as a superantigen.

As a potential mechanism for proteolysis, we considered the possibility that Int1p, like MMTV, might be cleaved by a proprotein convertase. A subset of serine endopeptidases, proprotein convertases cleave proproteins, or zymogens, to their active fragments by limited proteolysis at one or at most two specific cleave sites. In eukaryotes, these enzymes are called "subtilisin-like proprotein convertases" or SPC's. Most SPC's are autocatalytic and must be activated by cleavage of their propeptide before they can cleave their

| PBMC's FROM | TNFα (pg/ml) | | | IL-6 (pg/ml) | | | IL-4 (pg/ml) | | |
|---|---|---|---|---|---|---|---|---|---|
| | Day 2 | Day 4 | Day 6 | Day 2 | Day 4 | Day 6 | Day 2 | Day 4 | Day 6 |
| HIGH RESPONDER | | | | | | | | | |
| INT1+ *C. albicans* | 7014 | 746 | 841 | 10109 | 8726 | 19764 | <5 | <5 | <5 |
| Staphylococcal enterotoxin | 2143 | 631 | 102 | 3023 | 2459 | 2016 | 50 | 22 | 12 |
| LOW RESPONDER | Day 2 | Day 4 | Day 6 | Day 2 | Day 4 | Day 6 | Day 2 | Day 4 | Day 6 |
| INT1+ *C albicans* | 165 | 20 | ND | 7660 | 6820 | ND | <5 | <5 | <5 |
| Staphylococcal enterotoxin | 1963 | 667 | ND | 7850 | 7945 | ND | 89 | 20 | ND |

Identical Effects with *Saccharomyces cerevisiae* Expressing INT1

In order to assess these effects apart from other candidal antigens, we expressed INT1 in *S. cerevisiae* YPH500 under the control of a galactose-inducible promoter. INT1 was ligated into plasmid pBM272 for transformation of *S. cerevisiae* YPH 500; the resultant plasmid was named pCG01. Expression of Int1p was induced with 2% galactose. *S. cerevisiae* transformed with pBM272 served as control. Approximately 25% of donor PBMC's were activated after co-culture with *S. cerevisiae* expressing INT1, as measured by up-regulation of the IL-2 receptor on flow cytometry; no up-regulation occurred after co-culture with *S. cerevisiae* transformed with vector alone. These effects could be blocked by antibodies to HLA-DR. The Vβ2 subset was specific substrates. A model of a proprotein convertase is provided in FIG. 10, and the canonical cleavage site is indicated with an arrow.

Most proprotein convertases exhibit several highly conserved features including a propeptide domain, distinguished by a canonical cleavage site just C-terminal to a pair of dibasic amino acids, most frequently KR or KK. A catalytic domain spans approximately 330 amino acids with an active site sequent of D-H-N-S [Asp-His-Asn-Ser] (SEQ ID NO:3), in which the initiating D is followed by a DX. This DDX motif of the RGD tripeptide; however, this interaction has never been explored with proprotein convertases. Catalytic domains may occur singly or in tandem. Lastly, a processing domain (or P-domain) also contains a D-H-N-S (SEQ ID NO:3) motif, but in six of the seven know SPC's, an RGD tripeptide is intercalated between the N and the S. The RGD motif is essential for cleavage of the propeptide; site-directed mutagenesis of the RGD tripeptide inhibits zymogen processing and mis-directs cellular trafficking of the unprocessed protein.

In FIG. 11, a comparison of the Int1p sequence in *C. albicans* with the motifs essential for the proprotein convertases is shown, and this analysis disclosed several sites of interest, including a dibasic cleavage site at residue 263, two putative catalytic domains, and an RGD sequence correctly situation in a possible P domain. Regions recognized by specific rabbit anti-peptide polyclonal antibodies developed in our laboratory as shown in brackets.

Identification of an Amino-Terminal Peptide from Int1p in Activating Supernatants Subsequent experiments showed that the supernatants from exponentially replicating INT1/INT1 *C. albicans* or INT1-expressing *S. cerevisiae* were just as active as yeast cells in activating T lymphocytes, and all activity was contained in a pool of proteins weighing less than 50 kDa. Indeed, as little as 500 pmoles of supernatant proteins served to activate T lymphocytes.

Exposure of a Covert Amino-Terminal Domain in Int1p in the Presence of Heparin

Because colonization with *C. albicans* in the gastrointestinal tract does not induce superantigen-like effects, we hypothesized that some environmental factor relevant to fungemia might accelerate release of these <50 kDa amino-terminal polypeptides from Int1p. Heparin is known to enhance autocatalysis and to accelerate cleavage of a propeptide from a zymogen. These effects suggested that heparin might accelerate release of Int1p-derived fragments that might serve as superantigens. This possibility was all the more meaningful because heparin is an ever-present infusate in patients with intravascular catheters.

For these experiments, INT1/INT1 *C. albicans* blastospores were incubated in the absence or presence of heparin; flow cytometry with polyclonal antibodies to the second divalent cation binding site (anti-CBS2) or to the first 600 amino acids of the amino terminus (anti-INT600) was used to detect the appearance of these domains (see FIG. 11 for domains recognized by these antibodies).

Results: In the absence of heparin (FIG. 12—left panel), *C. albicans* blastospores displayed intensity fluorescence with anti-CBS2 (gray area) but did not fluoresce with anti-INT600. However with the addition of heparin, substantial fluorescence with anti-INT600 was now detectable (right panel). These results suggested that heparin exposed a covert amino-terminal domain and made it accessible for cleavage. If we were correct then a cleaved amino-terminal fragment of Int1p should be found in the supernatants of organisms grown in the presence of heparin but not in its absence.

Absence of Int1p Amino-Terminal Fragments in Culture Supernatants is Accelerated by Heparin FIG. 13 is a Western blot of supernatants from INT1-expressing *S. cerevisiae* grown in the absence or presence of heparin and probed with rabbit polyclonal antibodies to the Int1p amino terminus (anti-INT600), to the second divalent cation binding site (anti-CBS2), or to the RGD domain (anti-RGD).

Results: Supernatants probed with anti-CBS2 (panel 2) or anti-RGD (panel 3) showed identical banding patterns in the absence or presence of heparin. However, probing the supernatants with anti-INT600 disclosed two novel fragments of 27 kDa and 44 kDa only in the supernatants of organisms grown in the presence of heparin for three hours. In the absence of heparin, these fragments appeared at much reduced levels after 18 hours or more. Thus, heparin accelerated the appearance of two Int1p amino-terminal polypeptides in the supernatant. Supernatant containing the 27 and 44 kDa fragments activated T lymphocytes, while the other supernatants did not.

Localization of the Int1p Superantigen-like Fragment

From the foregoing experiments we had circumstantial evidence that amino-terminal fragments of Int1p (Mr 27 or 44 kDa) could be exposed in the presence of heparin, cleaved, and detected in the supernatant of INT-1expressing *S. cerevisiae*. If heparin accelerated the cleavage of Int1p by a proprotein convertase as occurs with the superantigen vSAG7 from MMTV, then an amino-terminal fragment encompassing 263 amino acids should be released from Int1p (FIG. 11). A preliminary estimate of the mass of the first 263 amino acids of Int1p was 35 kDa, rising to 42 kDa is glycosylated. We therefore tested the possibility that the first 263 amino acids of Int1p, hereinafter called $Pep_{263}$, constituted the superantigen-like moiety.

In order to obtain direct evidence that $Pep_{263}$ was responsible for the superantigen-like effects observed with INT1/INT1 *C. albicans* and INT1expressing *S. cerevisiae*, we expressed $Pep_{263}$ as a recombinant, His-tagged protein in *S. cerevisiae* and assessed its effects on T lymphocyte activation and expansion of Vβ subsets. *S. cerevisiae* was preferable to *E. coli* for expression in order to avoid the activating effects of lipopylsaccharide. *C. albicans* genomic DNA encoding amino acids 1 to 263 of Int1p was amplified by PCR and ligated in-frame to a 6X-His tage at the 3' end. This construct was inserted as a BamHI/Sa/I fragment into pBM272 and expressed from a galactose-inducible promoter in *S. cerevisiae* BJ3501, a protease-deficient strain. The His-tagged fusion protein appeared in the lysate (FIG. 14, lane 1). *S. cerevisiae* lysate was chromatographed on a nickel column, and an anti-His Mab was used in a dotblot to detect the His-tagged protein as it was eluted from a nickel column by an imidazole gradient (0–500 mM imidazole). The His-tagged $Pep_{263}$ eluted at a concentration of 300 mM imidazole in fractions 300-1 and 300-2 (FIG. 14, lanes 2 and 3). An additional filtration step yielded a single band of 44 kDa on silver strain (FIG. 14, lane 4), which reacted with anti-His antibody on Western (FIG. 14, lane 5). The use of these techniques has produced microgram quantities of the putative superantigen.

Activation of T Lymphocytes by Recombinant $Pep_{263}$ 100 picograms of $Pep_{263}$ was then incubated with $5 \times 10^6$ PBMC's in each of three reactions: (a) purified $Pep_{263}$ as a soluble peptide; (b) purified $Pep_{263}$ bound to the bottom of the tissue-culture well; (c) purified $Pep_{263}$ immobilized by anti-His antibodies covalently linked to Protein A Sepharose beads. Fractions which also eluted at 300 mM imidazole but contained no His-tagged protein were used as control.

Results: Unactivated T lymphocytes (left-most bar in each group of three) or T cells incubated with eluted peptides that did not contain the His tag (middle bar in each group of three) did not upregulate the IL-2 receptor. In contrast, as little as 100 picograms of soluble $Pep_{263}$ activated T lymphocytes (denoted with asterisk); up-regulation of the IL-2 receptor was two-fold higher than with control fractions. Substantial activation by $Pep_{263}$ occurred on day 3, one day sooner than had been observed with whole organisms (see FIG. 7). $Pep_{263}$ bound to the microtiter plate or immobilized by linkage to protein A beads failed to activate T lymphocytes. These results show that Pep$_{263}$ is capable of activating T lymphocytes to an extent that surpasses what we observed with whole *C. albicans* cells. Experiments to confirm that Pep$_{263}$ expands the Vβ2 subset are included in this proposal.

Model for the Participation of Int1p in Candidemia

We have presented preliminary evidence that the *C. albicans* protein Int1p exerts superantigen-like effects on human T lymphocytes. Activation of T lymphocytes as measured by up-regulation of the IL-2 receptor (CD25) is not dependent upon antigen processing and presentation, can be blocked by antibodies to MHC Class II, and results in the expansion of the Vβ2 subset. Activation of T lymphocytes can be triggered by Pep$_{263}$, a 263 amino acid peptide that is cleaved from the amino terminus of Int1p in a reaction accelerated by physiologic doses of heparin. Picogram inputs of Pep$_{263}$ are equivalent to INT1/INT1 *C. albicans* or INT1-expressing *S. cerevisiae* in the ability to activate T lymphocytes. Like most microbial superantigens, Pep$_{263}$ is active when soluble, not when bound to a microtiter plate or to antibody-coated beads.

FIG. 16 schematizes the apparent role of Int1p in *C. albicans* fungemia. In the absence of heparin (panel A), the first 263 amino acids of Int1p (Pep$_{263}$) are covert and cannot be detected by anti-INT600 antibodies (FIG. 12). Only in the presence of heparin (panel B) is the amino terminus of Int1p exposed, at which point Pep$_{263}$ is cleaved and released into the fluid phase (panel C), where it exerts superantigen-like effects culminating in the release of pro-inflammatory cytokines that influence the clinical outcome. While it is possible that there are other superantigens liberated by *C. albicans*, or that even smaller fragments of Pep$_{263}$ may also have superantigen-like effects, the activity of Pep$_{263}$ and the applicability of these interactions may be applicable to the problem of candidemia in the NICU infant.

What is claimed is:

1. An isolated monoclonal antibody that binds to the propeptide of the Int1p protein of *Candida albicans* wherein the propeptide consists of the amino acid residues 1–263 of the amino acid sequence of SEQ ID NO:1, wherein the monoclonal antibody has the ability to prevent cleavage of the propeptide from the Int1p protein, and the ability to inhibit T lymphocyte activation caused by *Candida albicans*.

2. Isolated antisera containing the monoclonal antibody according to claim 1.

3. A pharmaceutical composition comprising the isolated monoclonal antibody according to claim 1 and a physiologically acceptable carrier, vehicle or diluent.

4. A diagnostic kit comprising the isolated monoclonal antibody according to claim 1 and means for detecting binding by that antibody.

5. The isolated monoclonal antibody according to claim 1 wherein said monoclonal antibody is capable of inhibiting T lymphocyte activation in a host cell.

* * * * *